(12) United States Patent
Noshi et al.

(10) Patent No.: US 10,932,735 B2
(45) Date of Patent: Mar. 2, 2021

(54) NUCLEAR MEDICAL DIAGNOSTIC APPARATUS AND IMAGE PROCESSING METHOD

(71) Applicant: TOSHIBA MEDICAL SYSTEMS CORPORATION, Otawara (JP)

(72) Inventors: Yasuhiro Noshi, Otawara (JP);
Manabu Teshigawara, Otawara (JP);
Masahiro Kazama, Sakura (JP);
Tetsuya Sadotomo, Otawara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 522 days.

(21) Appl. No.: 14/984,792

(22) Filed: Dec. 30, 2015

(65) Prior Publication Data

US 2016/0113604 A1 Apr. 28, 2016

Related U.S. Application Data

(63) Continuation of application No. PCT/JP2014/068601, filed on Jul. 11, 2014.

(30) Foreign Application Priority Data

Jul. 11, 2013 (JP) .............................. JP2013-145766

(51) Int. Cl.
*A61B 6/00* (2006.01)
*A61B 8/08* (2006.01)
*A61B 6/03* (2006.01)

(52) U.S. Cl.
CPC ............ *A61B 6/4258* (2013.01); *A61B 6/032* (2013.01); *A61B 6/037* (2013.01); *A61B 6/4057* (2013.01);
(Continued)

(58) Field of Classification Search
None
See application file for complete search history.

(56) References Cited

U.S. PATENT DOCUMENTS

2003/0128801 A1 7/2003 Eisenberg et al.
2004/0190676 A1 9/2004 Kojima et al.
(Continued)

FOREIGN PATENT DOCUMENTS

JP 5-50386 U 7/1993
JP 2003-167058 6/2003
(Continued)

OTHER PUBLICATIONS

Watson et al., "A single scatter simulation technique for scatter correction in 3D PET". 1996, in the book of "Three-dimensional image reconstruction in radiation and nuclear medicine", pp. 255-268.*

(Continued)

*Primary Examiner* — Jeffrey G Hoekstra
*Assistant Examiner* — Yi-Shan Yang
(74) *Attorney, Agent, or Firm* — Oblon, McClelland, Maier & Neustadt, L.L.P.

(57) ABSTRACT

According to one embodiment, a nuclear medical diagnostic apparatus includes processing circuitry. The processing circuitry acquires gamma-ray emission data based on gamma rays emitted from radio isotopes administered to an object. The processing circuitry further executes scattered-ray correction on the gamma-ray emission data based on a second X-ray CT image obtained by replacing pixel values of a non-object region included in a first X-ray CT image with a predetermined pixel value.

11 Claims, 16 Drawing Sheets

(52) U.S. Cl.
CPC .............. *A61B 6/467* (2013.01); *A61B 6/481* (2013.01); *A61B 6/5205* (2013.01); *A61B 6/5235* (2013.01); *A61B 6/5282* (2013.01); *A61B 8/5207* (2013.01); *A61B 6/487* (2013.01); *A61B 6/488* (2013.01); *A61B 2576/00* (2013.01)

(56) References Cited

U.S. PATENT DOCUMENTS

| | | | | |
|---|---|---|---|---|
| 2006/0050943 | A1* | 3/2006 | Ozaki | A61B 6/032 382/131 |
| 2008/0224050 | A1* | 9/2008 | Thielemans | G01T 1/2985 250/362 |
| 2008/0310580 | A1* | 12/2008 | Takahashi | A61B 6/037 378/4 |
| 2009/0069672 | A1* | 3/2009 | Pfister | A61B 6/12 600/424 |
| 2010/0116994 | A1* | 5/2010 | Wollenweber | G01T 1/1611 250/363.03 |
| 2011/0058722 | A1* | 3/2011 | Hu | G06T 11/006 382/131 |
| 2011/0123074 | A1* | 5/2011 | Nie | G06T 5/008 382/128 |
| 2013/0127902 | A1* | 5/2013 | Zhu | G06T 7/12 345/620 |
| 2017/0079600 | A1* | 3/2017 | Bracken | A61B 6/12 |

FOREIGN PATENT DOCUMENTS

| | | | |
|---|---|---|---|
| JP | 2004-53494 | | 2/2004 |
| JP | 2004053494 | A * | 2/2004 |
| JP | 2005-514975 | | 5/2005 |
| JP | 2007-105221 | | 4/2007 |
| JP | 2007105221 | A * | 4/2007 |
| JP | 2008-267913 | | 11/2008 |
| JP | 2011-521224 | | 7/2011 |
| JP | 2011-220719 | | 11/2011 |

OTHER PUBLICATIONS

Histed et al., "Review of functional/anatomical Imaging in Oncology". Nucl Med Commun 2012; 33(4): 349-361.*
English translation of the International Preliminary Report on Patentability and Written Opinion dated Jan. 21, 2016 in PCT/JP2014/068601 filed Jul. 11, 2014.
International Search Report dated Sep. 22, 2014 in PCT/JP2014/068601 filed Jul. 11, 2014 (with English translation).

* cited by examiner

NUCLEAR MEDICAL DIAGNOSTIC APPARATUS AND IMAGE PROCESSING METHOD

CROSS-REFERENCE TO RELATED APPLICATIONS

This application is a Continuation application of No. PCT/JP2014/068601, filed on Jul. 11, 2014, and the PCT application is based upon and claims the benefit of priority from Japanese Patent Application No. 2013-145766, filed on Jul. 11, 2013, the entire contents of which are incorporated herein by reference.

FIELD

Embodiments described herein relate generally to a nuclear medical diagnostic apparatus and an image processing method.

BACKGROUND

Nuclear medicine diagnostic apparatuses use a property that a drug (a bloodstream marker, a tracer) containing radio isotopes (hereinafter, referred to as RIs) is selectively taken into a particular tissue or organ in a living body, and detect gamma rays emitted from the RIs distributed in the living body by means of gamma ray detectors provided outside of the living body.

Some of gamma rays emitted from RIs inside an object are generally scattered on their path inside the object by Compton scattering. These scattered gamma rays are also detected by a gamma-ray detector. As methods of eliminating the influence of scattered rays of this type, for example, a tail-fitting method, a DEW (Dual Energy Window) method, and a TEW (Triple Energy Window) method are included.

The tail-fitting method is a method of using gamma rays detected at a region, which is outside and around an object subjected to administration of RIs and in which any RI never exists (hereinafter, such a region is referred to as a non-object region). Gamma rays emitted from a non-object region appears in a tail region of a gamma-ray profile obtained from an object. Thus, the scattered-ray component can be estimated by approximating the tail region by a Gaussian distribution as an example.

When the tail-fitting method is used for scattered-ray correction, positional information on each non-object region in a nuclear medical image is required. The positional information on each non-object region can be estimated from an X-ray CT (Computed Tomography) image obtained by imaging the same region of the same object as the nuclear medical image, for example.

However, a region of atmospheric air and a region of some structure such as a top plate are both non-object regions (i.e., such a region that RIs never exists) but different in CT value from each other. Thus, when a pixel value corresponding to the CT value of atmospheric air (e.g., −1000 HU) is used for estimating each non-object region from an X-ray CT image, a top plate is not estimated as a non-object region. In this case, the non-object region estimated from the X-ray CT image becomes narrower on the top plate side of the object in the X-ray CT image than the actual non-object region by the top plate. Accordingly, data of a tail region are decreased by the top plate, which makes it difficult to appropriately execute scattered-ray correction by the tail-fitting method.

BRIEF DESCRIPTION OF THE DRAWINGS

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION

Hereinbelow, a description will be given of a nuclear medical diagnostic apparatus and an image processing method according to embodiments of the present invention with reference to the drawings. The nuclear medical diagnostic apparatus and the image processing method according to embodiments of the present invention can be applied to various devices configured to reconstruct an image based on dose distribution of gamma rays detected by a gamma-ray detector such as a SPECT (Single Photon Emission Computed Tomography) apparatus and a PET (Positron Emission Tomography) apparatus.

In general, according to one embodiment, a nuclear medical diagnostic apparatus includes processing circuitry. The processing circuitry acquires gamma-ray emission data based on gamma rays emitted from radio isotopes administered to an object. The processing circuitry further executes scattered-ray correction on the gamma-ray emission data based on a second X-ray CT image obtained by replacing pixel values of a non-object region included in a first X-ray CT image with a predetermined pixel value.

First Embodiment

Figure 1:
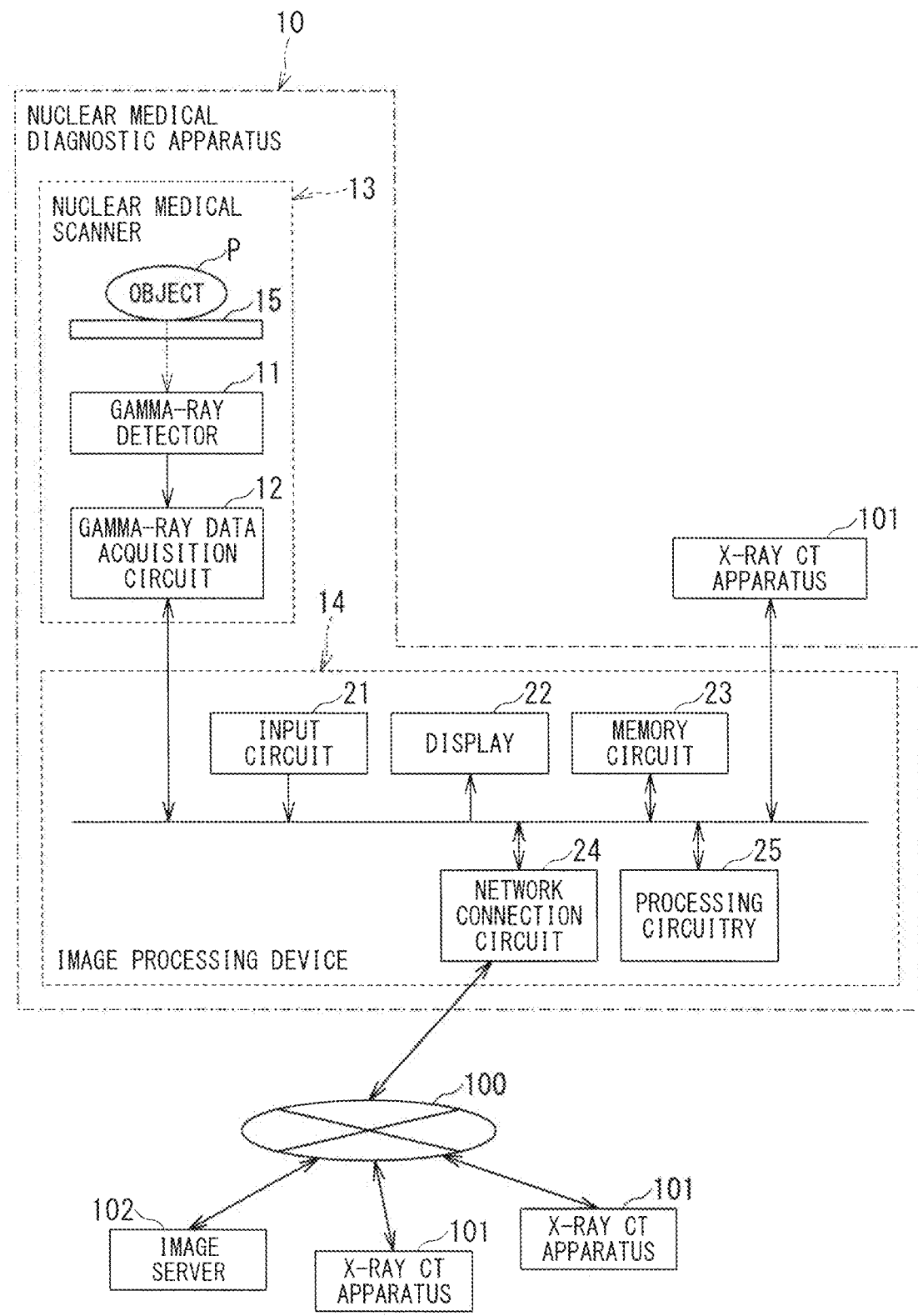
FIG. 1 is a block diagram showing an example of overall configuration of a nuclear medical diagnostic apparatus in the first embodiment.

FIG. 1 is a block diagram showing an example of overall configuration of a nuclear medical diagnostic apparatus 10 in the first embodiment. The nuclear medical diagnostic apparatus 10 of the present embodiment is configured to be able to acquire X-ray CT images generated by an X-ray CT apparatus 101.

The nuclear medical diagnostic apparatus 10 includes an image processing device 14 and a nuclear medical scanner 13 equipped with a gamma-ray detector 11 and a gamma-ray data acquisition circuit 12. It is enough that the image processing device 14 is connected to the gamma-ray data acquisition circuit 12 so as to be able to transmit and receive data to/from the gamma-ray data acquisition circuit 12. Thus, the image processing device 14 is not necessarily required to be installed in the same room or building as the gamma-ray data acquisition circuit 12.

The gamma-ray detector 11 detects gamma rays emitted from radio isotopes in a predetermined imaging region of an object P loaded on a top plate 15, under the control of the image processing device 14.

When a SPECT apparatus is used as the nuclear medical diagnostic apparatus 10, the gamma-ray detector 11 is a detector configured to detect gamma rays emitted from radio isotopes such as technetium included in medical agent administered to the object P. A scintillator type detector and/or a semiconductor type detector may be used as the gamma-ray detector 11.

When the gamma-ray detector 11 is configured using a scintillator type detector, the gamma-ray detector 11 includes, for example, a collimator for defining an entrance angle of gamma rays, a scintillator configured to instantaneously flash when collimated gamma rays enter the gamma-ray detector 11, a light guide, two-dimensionally arranged photomultiplier tubes for detecting light emitted from the scintillator, and an electronic circuit for the scintillator. The scintillator is configured of Thallium doped Sodium Iodide NaI(TI), for example.

Each time an event of gamma ray entrance occurs, the electronic circuit for the scintillator generates entrance position information (i.e., positional information) and intensity information of gamma rays within a detection plane configured of the plurality of photomultiplier tubes, based on outputs of the plurality of photomultiplier tubes, and outputs the generated information to the gamma-ray data acquisition circuit 12. The above positional information may be two-dimensional coordinate information in the detection plane. Additionally, under the premise that the detection plane is virtually divided into plural, e.g., 1024-by-1024 regions (hereinafter, referred to as primary cells) in advance, the above positional information may be information indicating which primary cell gamma rays entered.

On the other hand, when the gamma-ray detector 11 is configured using a semiconductor type detector, the gamma-ray detector 11 includes, for example, a collimator, two-dimensionally arranged semiconductor devices for detecting collimated gamma rays (hereinafter, shortly referred to as semiconductor devices), and an electronic circuit for semiconductor. Each of the semiconductor devices is configured of, for example, CdTe (Cadmium Telluride) and/or CdZnTe (Cadmium Zinc telluride or CZT).

Each time an event of gamma ray entrance occurs, the electronic circuit for semiconductor generates positional information and intensity information of the gamma rays based on output of each of the semiconductor devices and outputs the generated information to the gamma-ray data acquisition circuit 12. This positional information indicates which of the plural (e.g., 1024-by-1024) semiconductor devices the gamma rays entered.

In addition, when a PET apparatus is used as the nuclear medical diagnostic apparatus 10, the gamma-ray detector 11 is a detector configured to detect gamma rays emitted from radio isotopes included in medical agent such as FDG (fluoroDeoxyGlucose) administered to the object P. Also in this case, a scintillator type detector and/or a semiconductor type detector may be used as the gamma-ray detector 11, and configuration of a scintillator type detector and configuration of a semiconductor type detector are similar to the case of using a SPECT apparatus as the nuclear medical diagnostic apparatus 10 as mentioned above.

When a PET apparatus is used as the nuclear medical diagnostic apparatus 10, plural detection elements of the gamma-ray detector 11 are, for example, hexagonally-arranged or circularly-arranged inside its detector cover so as to surround the circumference of the object P.

How to arrange the plurality of detection elements is not limited to the ring-like arrangement, and may be, for example, two-detector-group opposing arrangement. In the two-detector-group opposing arrangement, two groups of the plurality of detection elements respectively arranged on flat plates are arranged so as to be opposed to each other with the patient O being sandwiched therebetween, and are rotatably held around the patient O. The plurality of detection elements may be arranged in multi-layer rings so as to be capable of acquiring images between adjacent layers.

In other words, the gamma-ray detector 11 detects gamma rays emitted from radio isotopes of a predetermined imaging region of the object P under the control of the image processing device 14, and outputs positional information and intensity information for each event. In addition, the positional information is at least one of information indicating which position of primary cells gamma rays entered and two-dimensional coordinate information indicating which position in the detection plane gamma rays entered. Hereinafter, an example of a case where the gamma-ray detector 11 outputs positional information indicating position in the detection plane where gamma rays entered will be explained.

The gamma-ray data acquisition circuit 12 acquires output of the gamma-ray detector 11 in a list mode as an example, and outputs the acquired data to the image processing device 14 as the gamma-ray emission data. In the list mode, detection position information on a gamma ray, intensity (energy) information, information indicating a relative position between the gamma-ray detector 11 and the patient O (a position and angle of the gamma-ray detector 11), and detection time of the gamma ray are collected each time a gamma ray entrance event occurs.

The image processing device 14 includes an input circuit 21, a display 22, a memory circuit 23, a network connection circuit 24, and processing circuitry 25 as shown in FIG. 1.

The input circuit 21 includes at least a pointing device and is configured of general input devices such as a mouse, a trackball, a keyboard, a touch panel, and a numerical keypad. The input circuit 21 outputs an operational input signal corresponding to a user's operation to the processing circuitry 25.

The display 22 is configured of a general display output device such as a liquid crystal display and an OELD (Organic Light Emitting Diode), and displays various types of image such as an X-ray CT image and a nuclear medical image under the control of the processing circuitry 25.

The memory circuit 23 includes memory media readable by a processor such as a magnetic memory medium, an optical memory medium, and a semiconductor memory. The memory circuit 23 may be configured so that some or all of the programs and data stored in these memory media can be downloaded via an electronic network. The memory circuit 23 stores count values of respective pixels, plural types of look-up table (LUT) associating count values with respective pixel values indicative of color and/or luminance, and template shape information of the top plate 15, under the control of the processing circuitry 25.

The network connection circuit 24 implements various types of information-communication protocols according to the aspect of the network 100. The network connection circuit 24 connects the image processing device 14 to other electric equipments via the network 100 according to those various types of protocols. The above-described network 100 means a general information communication network using telecommunications technology and includes a telephone communication network, an optical fiber communication network, a cable communication network, and a satellite communication network in addition to Internet network and a wireless/wired LAN (Local Area Network) such as a hospital LAN.

The image server 102 is a server for long-term storage of images installed in a PACS (Picture Archiving and Communication System) as an example, and stores medical images generated by other modalities such as the X-ray CT apparatus 101 interconnected via the network 100.

The processing circuitry 25 is configured of circuit elements such as a processor and memory media including a RAM (Random Access Memory) and a ROM (Read-Only Memory), and controls operations of the image processing device 14 according to the programs stored in those memory media.

The processor of the processing circuitry 25 loads an image processing program stored in one of the memory media including the ROM and data necessary for executing this program to the RAM, and executes processing necessary for appropriate scattered-ray correction by the tail-fitting method using a non-object region accurately estimated from an X-ray CT image according to this program.

The above-described non-object region means such a region around the object P that any RI is not supposed to exist. As examples of the above-described non-object region, the region of the top plate 15 and a region of air (i.e., atmospheric air) are included.

The RAM of the processing circuitry 25 provides a work area for temporarily storing data and programs executed by the processor. The memory media of the processing circuitry 25 including the ROM store a boot program of the image processing device 14, an image processing program, and various types of data necessary for executing those programs. The memory medium typified by the ROM may include a recording medium readable by the processor, such as a magnetic or optical recording medium or a semiconductor memory, and the entirety or a part of the programs and the data in the memory medium may be downloaded via an electronic network.

Figure 2:
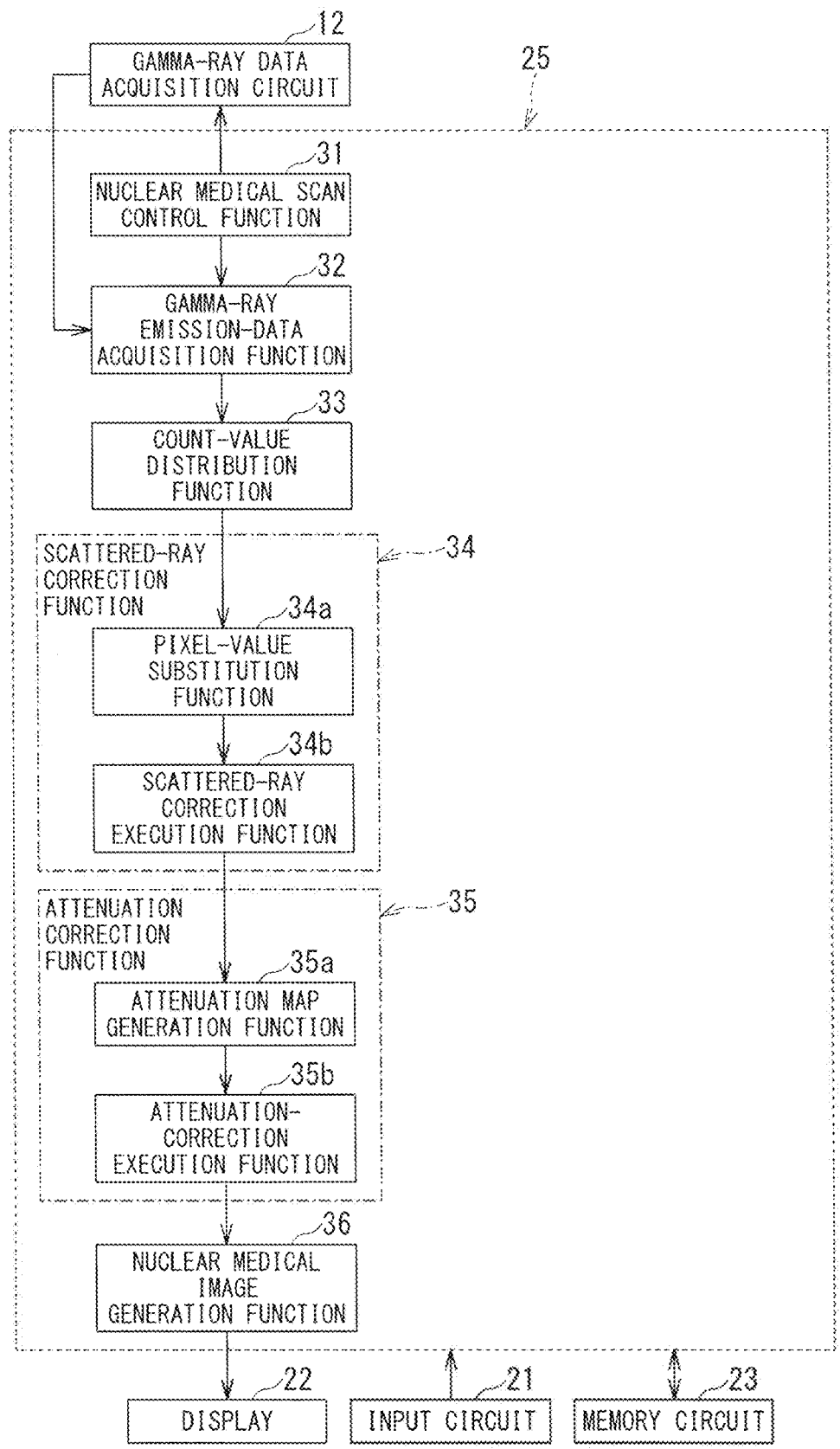
FIG. 2 is a general block diagram showing an example of functions implemented by a processor of processing circuitry in the first embodiment.

FIG. 2 is a general block diagram showing an example of functions implemented by a processor of the processing circuitry 25 in the first embodiment;

As shown in FIG. 2, the processor of the processing circuitry 25 functions as at least a nuclear medical scan control function 31, a gamma-ray emission-data acquisition function 32, a count-value distribution function 33, a scattered-ray correction function 34, an attenuation correction function 35, and a nuclear medical image generation function 36, by image processing programs stored in the memory media including the ROM. Each of these functions is stored in the form of program in a memory medium.

The nuclear medical scan control function 31 receives a command to execute a scan plan entered by a user via the input circuit 21, and causes the nuclear medical scanner 13 to execute a scan based on the scan plan. As a result, information on gamma rays emitted from the object P is inputted from the gamma-ray detector 11 to the gamma-ray emission-data acquisition function 32 via the gamma-ray data acquisition circuit 12.

The gamma-ray emission-data acquisition function 32 acquires the gamma-ray emission data based on gamma rays emitted from RIs administered to the object P. The gamma-ray emission data include detection position information on a gamma ray, intensity information, information indicating a relative position between the gamma-ray detector 11 and the patient O (a position and angle of the gamma-ray detector 11), and detection time of the gamma ray.

The count-value distribution function 33 associates display pixels of the display 22 with entrance position information of gamma rays, and calculates a count value for each of the display pixels by counting photon number of gamma rays entering each display pixel. Then, the count-value distribution function 33 assigns, i.e., distributes the calculated count value to each display pixel.

The scattered-ray correction function 34 includes a pixel-value substitution function 34a and a scattered-ray correction execution function 34, and executes scattered-ray correction on the gamma-ray emission data by the tail-fitting method based on an X-ray CT image.

The scattered-ray correction executed by the scattered-ray correction function 34 will be explained as follows.

Figure 3:
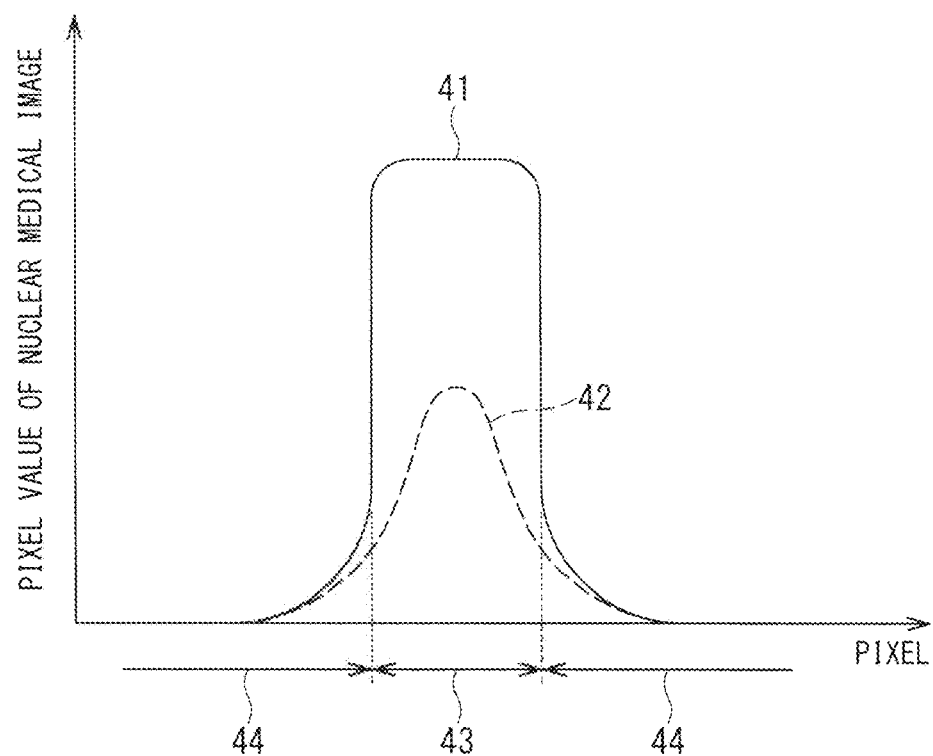
FIG. 3 is an explanatory diagram showing an example of relationship between pixel-value distribution of a nuclear medical image and scattered-ray distribution estimated from this pixel-value distribution.

FIG. 3 is an explanatory diagram showing an example of relationship between pixel-value distribution 41 of a nuclear medical image and scattered-ray distribution 42 estimated from the pixel-value distribution 41.

Each pixel of a nuclear medical image has a pixel value according to a count value associated with this pixel.

As shown in FIG. 3, the pixel-value distribution 41 of a nuclear medical image has its peak at an object region 43 derived from the object P and has tail regions (i.e., scattering regions) in the non-object region 44. Each of the tail regions has such a distribution that its pixel value gradually approaches zero as it is more separated from the object region 43.

In the so-called tail-fitting method, the scattered-ray distribution 42 is estimated by approximating each tail region (i.e., each scattering region where any radioactivity distribution is not supposed to exist) by the Gaussian distribution and then scattered-ray correction is executed based on the scattered-ray distribution 42. In more detail, information on absolute values is necessary for executing the scattered-ray correction in addition to shape information of the scattered-ray distribution 42. As a method of determining absolute values, a method of extracting an outline of the object P for each angle on a sinogram obtained by forward projection of a nuclear medical image and then executing the tail-fitting method by regarding values outside the extracted outline as values of scattered rays can be considered.

Meanwhile, since a count value of a nuclear medical image is low in general, much noise is included in each count value. Thus, it is difficult to extract the outline of the object P from a sinogram of a nuclear medical image. For the above reason, when the outline of the object P is extracted in the tail-fitting method, a sinogram obtained by forward projection of an X-ray CT image is used in many cases.

As to the same object for which the gamma-ray emission data are obtained, an X-ray CT image preliminarily generated by the X-ray CT apparatus 101 for substantially the same region as the above gamma-ray emission data is referred to as the first X-ray CT image 51 in the following explanation.

Figures 4A, 4B:
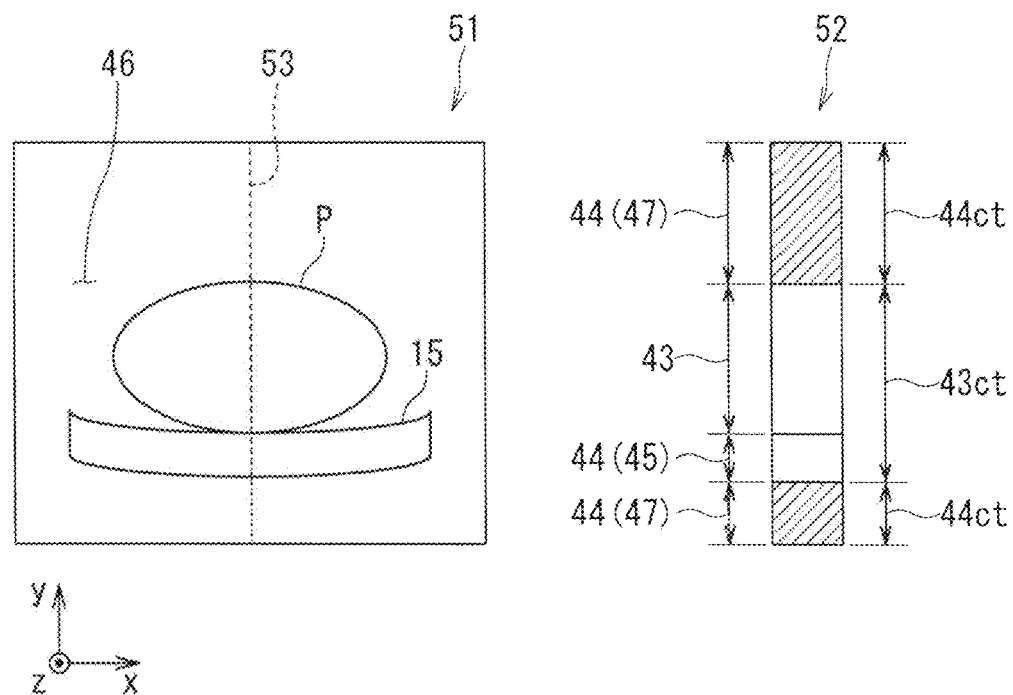
FIG. 4A is an explanatory diagram showing an example of the first X-ray CT image.
FIG. 4B is an explanatory diagram showing an example of one-dimensional data of a sinogram obtained by forward projection of the first X-ray CT image.

FIG. 4A is an explanatory diagram showing an example of the first X-ray CT image 51 and FIG. 4B is an explanatory diagram showing an example of a sinogram 52 obtained by forward projection of the first X-ray CT image. Hereinafter, an example of a case where the first X-ray CT image 51 is composed of an image region of the object P, an image region of the top plate 15, and an image region of air 46 will be explained. In addition, FIG. 4B shows an example of the sinogram 52 at the predetermined angle corresponding to the broken line 53 of the first X-ray CT image 51 in FIG. 4A.

Further, in the following explanation, it is assumed that the body axis direction of the object P is the z-axis direction, the width direction of the object P in parallel with the top and bottom surfaces of the top plate 15 is the x-axis direction, and the direction of the normal line of the top and bottom surfaces of the top plate 15 is the y-axis direction.

Gamma rays are never counted from a region where any RI does not exist, except scattered rays. Thus, in the pixel-value distribution 41 of a nuclear medical image, the non-object region 44 is simply a region excluding the object P, and the non-object region 44 includes, for example, a region 45 of the top plate 15 and a region 47 of air (e.g., atmospheric air) 46. Hereinafter, the region 45 of the top plate 15 is simply referred to as a top plate region 45 and the region 47 of the air 46 is simply referred to as an air region.

The top plate region 45 and the air region 47 commonly belong to the non-object region 44 but are different in CT value from each other. Thus, the top plate region 45 and the air region 47 are different in pixel value of an X-ray CT image from each other. For example, when a region having pixel values corresponding to the CT value (i.e., −1000 HU) of the air 46 in an X-ray CT image is defined as a non-object region 44ct and the remaining region is defined as an object region 43ct, the non-object region 44ct in the sinogram 52 corresponding to the first X-ray CT image 51 becomes different in the image region corresponding to the top plate region 45 from the actual non-object region (see FIG. 4B).

In this case, the non-object region 44ct estimated from the first X-ray CT image 51 becomes narrower on the top plate 15 side of the object P in the first X-ray CT image 51 than the actual non-object region by the top plate 15. Thus, data of the tail regions (i.e., scattering regions) are lessened by the data amount corresponding to the top plate region 45, which makes it difficult to appropriately execute scattered-ray correction by the tail-fitting method.

Figure 5A:
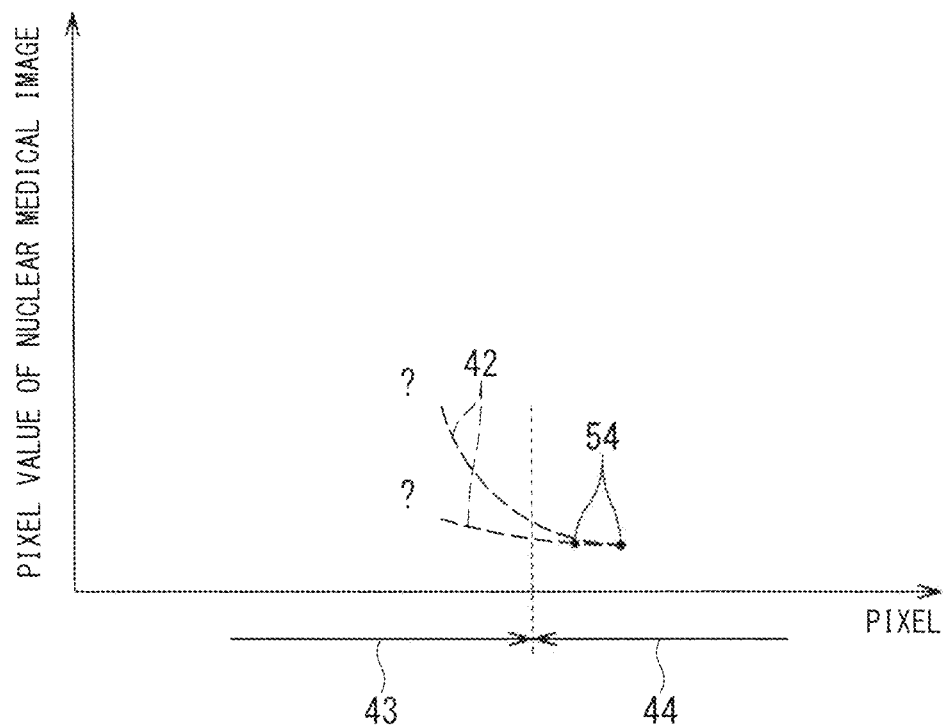
FIG. 5A is an explanatory diagram showing an example of a process of estimating scattered-ray distribution when the number of plots in a tail region is insufficient.

FIG. 5A is an explanatory diagram showing an example of a process of estimating the scattered-ray distribution 42 when the number of plots 54 in a tail region is insufficient.

Figure 5B:
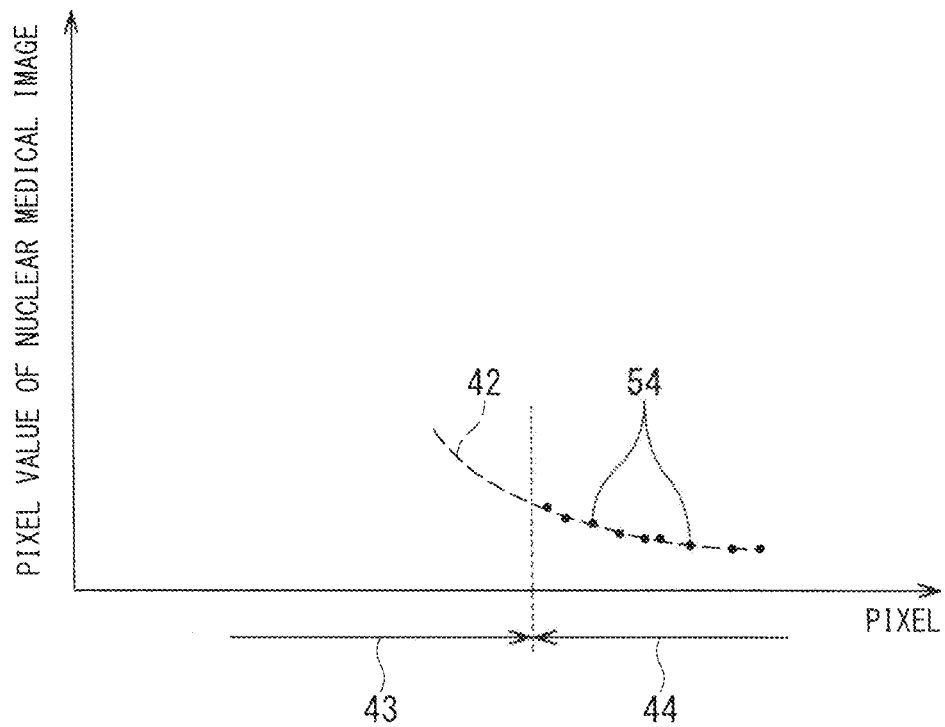
FIG. 5B is an explanatory diagram showing an example of a process of estimating scattered-ray distribution when the number of plots in a tail region is sufficient.

FIG. 5B is an explanatory diagram showing an example of a process of estimating the scattered-ray distribution 42 when the number of plots 54 in a tail region is sufficient.

As shown in FIG. 5A, when the number of pixels in a tail region is not sufficient for the tail-fitting method, it is difficult to estimate the scattered-ray distribution 42 and estimate accuracy of absolute values of scattered trays is reduced. Thus, in order to accurately estimate the scattered-ray distribution 42 in the tail-fitting method, it is important that sufficient number of pixels (i.e., pixel values) exist in a tail region as shown in FIG. 5B.

However, as shown in FIG. 4B, the non-object region 44ct estimated based on the first X-ray CT image 51 in which an image region of the top plate 15 is included becomes narrower than the actual non-object region 44 by the top plate region 45. Thus, when scattered-ray correction of nuclear medical data is executed after extracting the outline of the object P (i.e., the border between the object region 43ct and the non-object region 44ct) based on the object region 43ct and the non-object region 44ct estimated from the first X-ray CT image 51, pixel number of the tail region becomes insufficient and estimate accuracy of the scattered-ray distribution 42 is reduced.

For this reason, the pixel-value substitution function 34a of the scattered-ray correction function 34 generates the second X-ray CT image 61 subjected to pixel value substitution, by replacing pixel values of a non-object region included in a first X-ray CT image 51 with a predetermined pixel value, i.e., by substituting a predetermined pixel value for each pixel value of each predetermined non-object region included in the first X-ray CT image 51 such as the top plate region 45. As the above-described predetermined pixel value, for example, a pixel value corresponding to an HU value −1000 of the air 46 may be used.

Figure 6A:
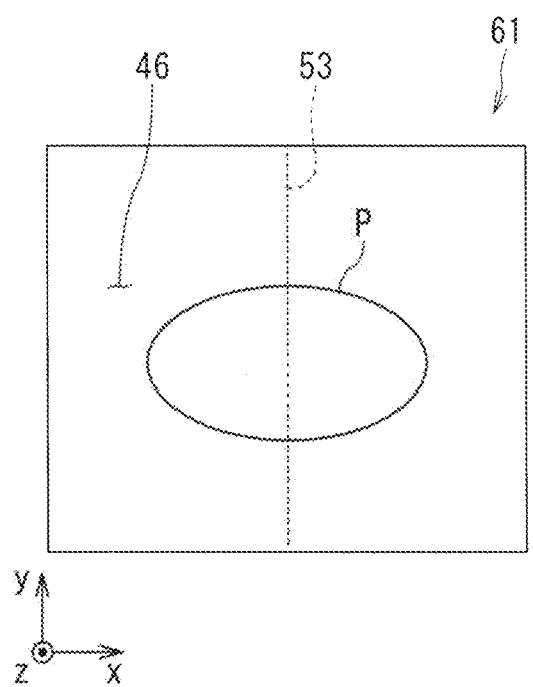
FIG. 6A is an explanatory diagram showing an example of the second X-ray CT image.
Figure 6B:
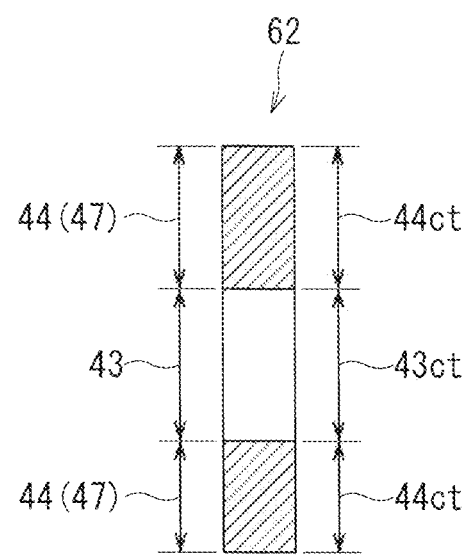
FIG. 6B is an explanatory diagram showing an example of a sinogram obtained by forward projection of the second X-ray CT image.

FIG. 6A is an explanatory diagram showing an example of the second X-ray CT image 61. FIG. 6B is an explanatory diagram showing an example of a sinogram 62 (i.e., forward projection data as one dimensional data) obtained by forward projection of the second X-ray CT image 61. FIG. 6A shows an example of the second X-ray CT image 61 generated by the pixel-value substitution function 34a in such a manner that pixel values of the air 46 are substituted for pixel values of respective pixels of the top plate region 45 in the first X-ray CT image 51. In addition, FIG. 6B shows an example of the sinogram 62 at the predetermined angle corresponding to the broken line 53 in the second X-ray CT image 61 shown in FIG. 6A.

As shown in FIG. 6B, since the top plate region 45 does not exist in the non-object region 44ct estimated based on the second X-ray CT image 61 obtained by substituting a pixel value of the air 46 for each pixel value of the top plate region 45, such a non-object region 44ct becomes equal to the actual non-object region 44. Thus, with the use of the second X-ray CT image 61, the non-object region 44 can be accurately estimated. Hence, when the outline of the object P extracted based on the second X-ray CT image 61 is used, more pixels in each tail region (scattered-ray region) can be obtained than the case of using the outline of the object P extracted based on the first X-ray CT image 51, and thus scattered-ray correction can be more appropriately executed by the tail-fitting method.

Specifically, the pixel-value substitution function 34a extracts the outline of the object P for each cross-section of the second X-ray CT image 61 (FIG. 6A), then generates the sinogram 62 (i.e., forward projection data as one-dimensional data) by performing forward projection based on the extracted outline information, and then outputs the sinogram 62 to the scattered-ray correction execution function 34b. In addition, the pixel-value substitution function 34a may extract the outline of the object P by extracting the border between the object region 43ct and the non-object region 44ct from the sinogram 62 obtained by forward projection of the second X-ray CT image 61.

Incidentally, when the X-ray CT apparatus 101 has a function equivalent to the pixel-value substitution function 34a, the nuclear medical diagnostic apparatus 10 may not be provided with the pixel-value substitution function 34a.

The scattered-ray correction execution function 34b executes scattered-ray correction on the gamma-ray emission data by the tail-fitting method based on the second X-ray CT image 61 (i.e., an X-ray CT image subjected to pixel value substitution).

The attenuation correction function 35 includes an attenuation map generation function 35a and an attenuation-correction execution function 35b. The attenuation correction function 35 executes attenuation correction on the gamma-ray emission data based on a gamma-ray attenuation coefficient map of the object P generated by using pixel values of the object region depicted in the first X-ray CT image 51 or the second X-ray CT image 61.

Gamma rays are attenuated inside a living body. Thus, an effect of attenuation inside a living body is included in a detection result of gamma rays. As a method frequently used for correcting the effect of this type of attenuation inside a living body, a method of generating a gamma-ray attenuation coefficient map (hereinafter, shortly referred to as an attenuation map) indicative of distribution of attenuation coefficients of gamma-ray energy of used nuclide and correcting a detection result of gamma rays based on this attenuation map is known. According to this method, the effect of attenuation of gamma rays inside a living body can be corrected (hereinafter, referred to as "execute/executing attenuation correction"). Thus, a nuclear medical image can be more accurately generated than a case where attenuation correction is not executed.

The attenuation map generation function 35a generates the gamma-ray attenuation coefficient map, i.e., attenuation map of the object P by executing Hu-Mu conversion with the use of pixel values of the object region depicted in the first X-ray CT image 51 (or the second X-ray CT image 61). The above-described Hu-Mu conversion is processing of converting a CT value (i.e., HU value) of each pixel of an X-ray CT image into a linear attenuation coefficient in order to generate an attenuation map. As methods of the Hu-Mu conversion, various conventional methods are known and any one of them can be used.

The nuclear medical diagnostic apparatus 10 may not be provided with the attenuation map generation function 35a, when an attenuation map can be obtained without generating it (e.g., when the X-ray CT apparatus 101 has a function equivalent to the attenuation map generation function 35a, when an attenuation map can be acquired via the network 100, and when an attenuation map is preliminarily stored in the memory circuit 23).

The attenuation-correction execution function 35b executes attenuation correction on the gamma-ray emission data based on an attenuation map.

The nuclear medical image generation function 36 generates a nuclear medical image by calculating pixel values indicative of color and/or luminance of respective display pixels. This calculation of pixel values is executed based on one of LUTs stored in the memory circuit 23 (e.g., an LUT being set as default to be used in a case where a specific LUT is not designated by a user), with the use of each count value subjected to scattered-ray correction by the scattered-ray correction function 34 and attenuation correction by the attenuation correction function 35. Then, the nuclear medical image generation function 36 causes the display 22 to display the generated nuclear medical image.

Figure 7A:
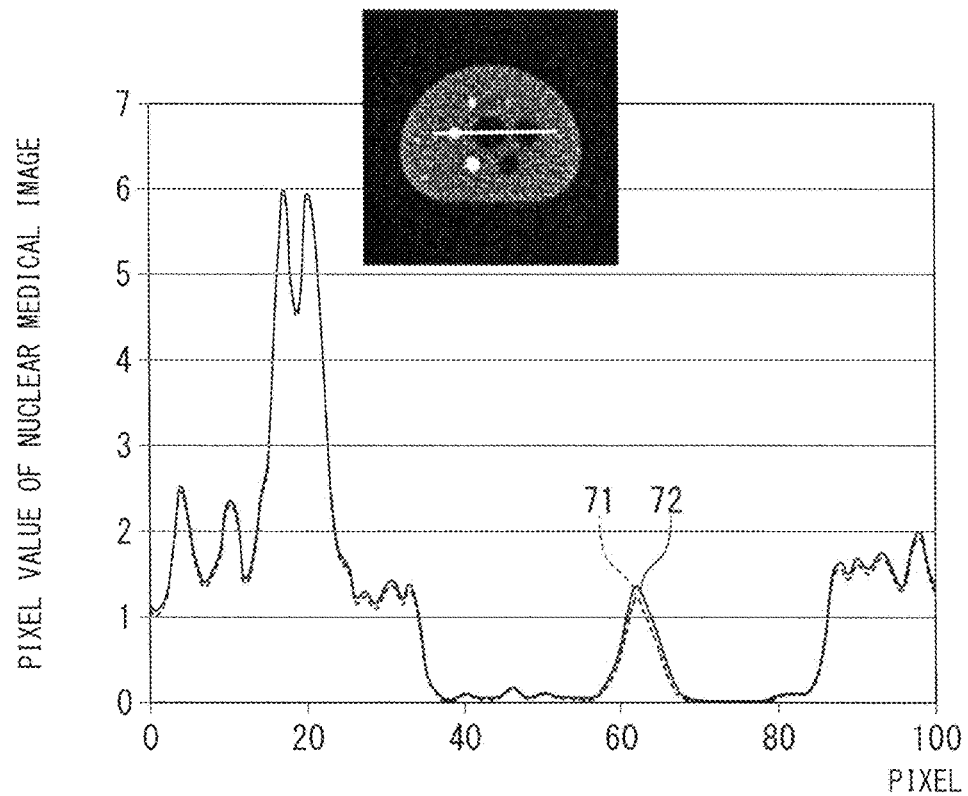
FIG. 7A is an explanatory diagram showing comparison between pixel values of a nuclear medical image subjected to scattered-ray correction based on the first X-ray CT image and pixel values subjected to scattered-ray correction based on the second X-ray CT image, in the first cross-section of a predetermined phantom.

FIG. 7A is an explanatory diagram showing comparison between pixel values 71 of a nuclear medical image subjected to scattered-ray correction based on the first X-ray CT image 51 and pixel values 72 subjected to scattered-ray correction based on the second X-ray CT image 61, in the first cross-section of a predetermined phantom.

Figure 7B:
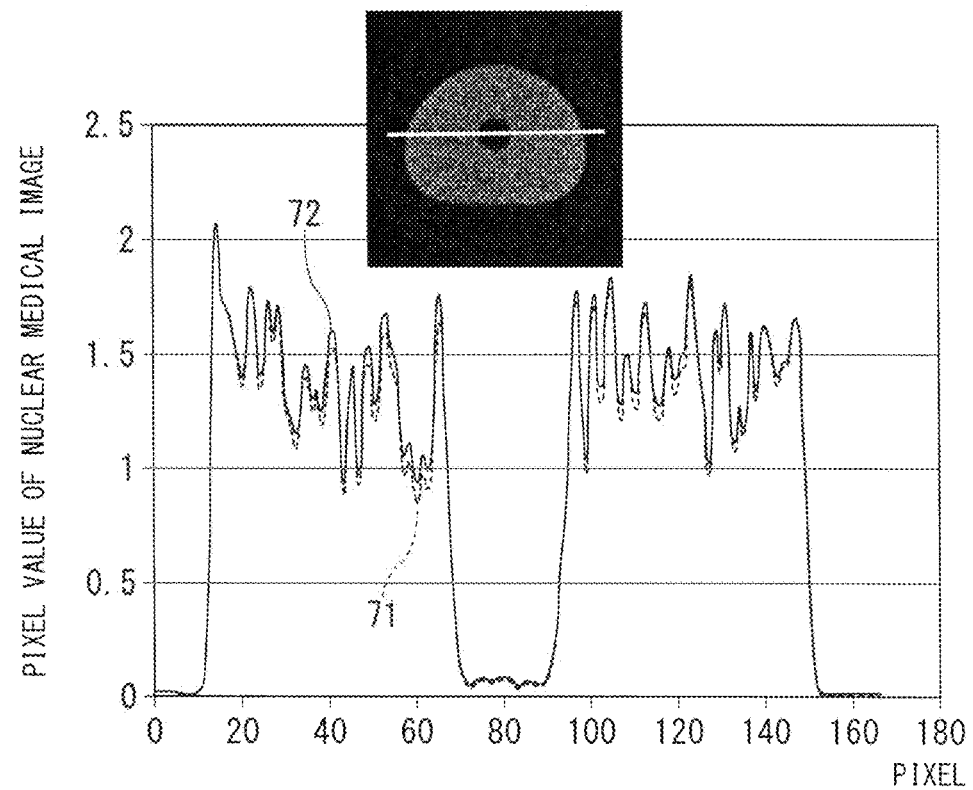
FIG. 7B is an explanatory diagram showing comparison between pixel values of a nuclear medical image subjected to scattered-ray correction based on the first X-ray CT image and pixel values subjected to scattered-ray correction based on the second X-ray CT image, in the second cross-section of the predetermined phantom.

FIG. 7B is an explanatory diagram showing comparison between pixel values 71 of a nuclear medical image subjected to scattered-ray correction based on the first X-ray CT image 51 and pixel values 72 subjected to scattered-ray correction based on the second X-ray CT image 61, in the second cross-section of the predetermined phantom.

As shown in FIG. 7A and FIG. 7B, the pixel values 72 of the nuclear medical image subjected to scattered-ray correction based on the second X-ray CT image 61 have higher contrast as a whole than the pixel values 71 of the same nuclear medical image subjected to scattered-ray correction based on the first X-ray CT image 51. Thus, according to a nuclear medical image subjected to scattered-ray correction based on the second X-ray CT image 61, image quality is improved, quantitative property is improved, and thereby diagnostic efficiency based on a nuclear medical image is improved.

Next, an example of an operation executed by the nuclear medical diagnostic apparatus 10 of the present embodiment will be explained.

Figure 8:
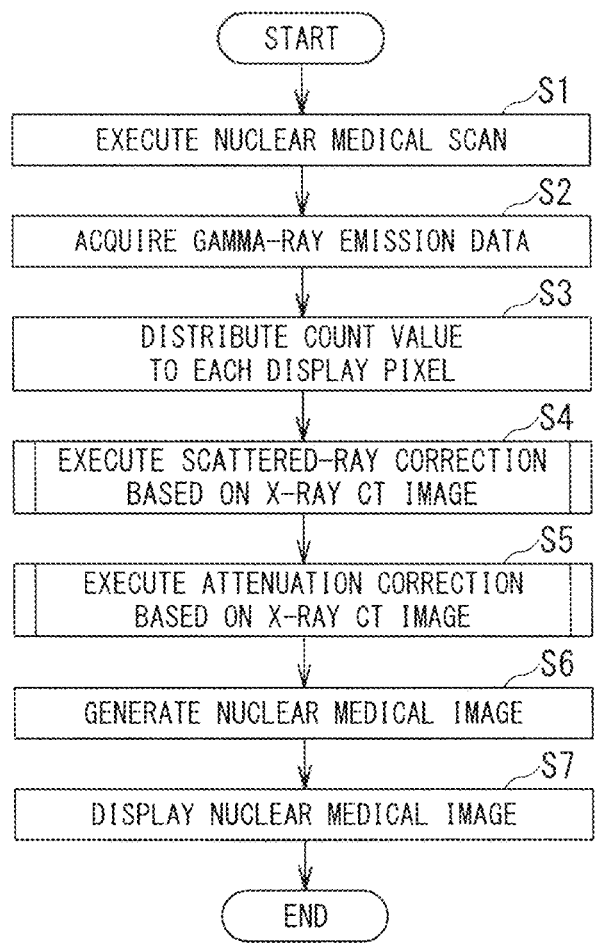
FIG. 8 is a flowchart showing appropriate scattered-ray correction by the tail-fitting method with the use of a non-object region accurately estimated from the second X-ray CT image executed by the processor of the processing circuitry shown in FIG. 1.

FIG. 8 is a flowchart of appropriate scattered-ray correction under the tail-fitting method with the use of the non-object region 44ct accurately estimated from the second X-ray CT image 61 executed by the processor of the processing circuitry 25 shown in FIG. 1. In FIG. 8, each symbol in which number is added on the right side of S indicates its step number of the flowchart.

First, in the step S1, the nuclear medical scan control function 31 receives a command to execute a scan plan from a user via the input circuit 21 and controls the nuclear medical scanner 13 so that a scan is executed based on the scan plan.

Next, in the step S2, the gamma-ray emission-data acquisition function 32 acquires the gamma-ray emission data based on gamma rays emitted from RIs administered to the object.

Next, in the step S3, the count-value distribution function 33 calculates positional correspondence between respective display pixels of the display 22 and entrance position information of gamma rays, and calculates a count value for each of the display pixels by counting photon number of gamma rays entering each display pixel. Then, the count-value distribution function 33 distributes the calculated count values to respective display pixels and stores this distribution information in the memory circuit 23.

Next, in the step S4, the scattered-ray correction function 34 executes scattered-ray correction on each count value by the tail-fitting method based on information on the outline of the object P estimated from the second X-ray CT image 61 (i.e., information on the non-object region 44ct).

Next, in the step S5, the attenuation correction function 35 executes attenuation correction on each count value according to the attenuation map generated based on the first X-ray CT image 51 or the second X-ray CT image 61.

Next, in the step S6, the nuclear medical image generation function 36 generates a nuclear medical image by using each count value subjected to both scattered-ray correction by the scattered-ray correction function 34 and attenuation correction by the attenuation correction function 35.

Then, in the step S7, the nuclear medical image generation function 36 causes the display 22 to display the generated nuclear medical image.

According to the above procedure, scattered-ray correction can be appropriately executed by the tail-fitting method with the use of the non-object region 44ct accurately estimated from the second X-ray CT image 61.

Figure 9:
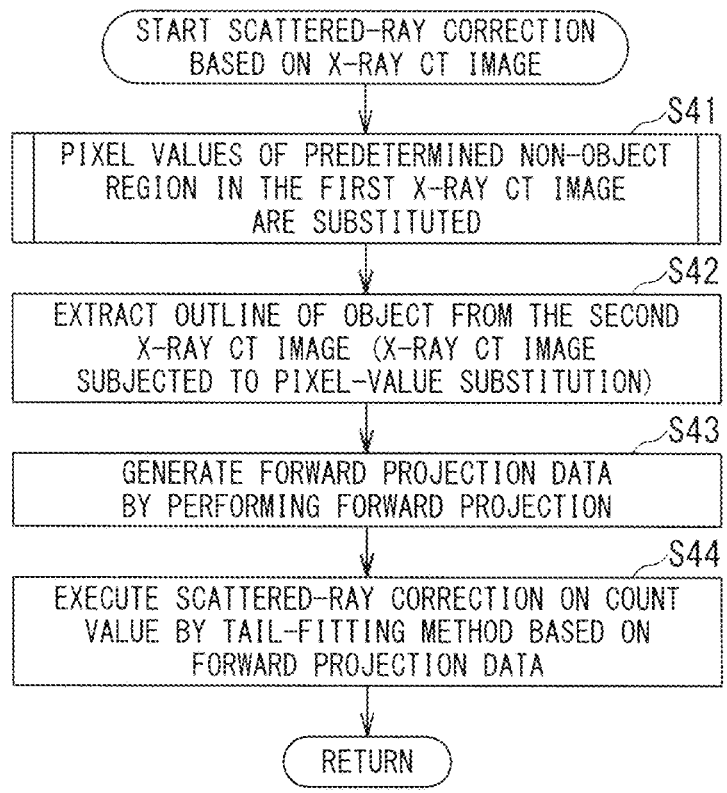
FIG. 9 is a subroutine flowchart of the scattered-ray correction in the step S4 of FIG. 8 executed by a scattered-ray correction function based on the second X-ray CT image.

FIG. 9 is a subroutine flowchart of the scattered-ray correction in the step S4 of FIG. 8 executed by the scattered-ray correction function 34 based on the second X-ray CT image 61.

This subroutine starts when the nuclear medical diagnostic apparatus 10 acquires the first X-ray CT image 51 from the X-ray CT apparatus 101. Incidentally, the first X-ray CT image 51 may be acquired from the X-ray CT apparatus 101 prior to start of the processing shown in FIG. 8 and be preliminarily stored in the memory circuit 23, for example.

In the step S41, the pixel-value substitution function 34a executes the pixel-value substitution so as to generate the second X-ray CT image 61, by substituting the predetermined pixel value (e.g., a pixel value corresponding to an HU value −1000 of the air 46) for pixel values of the predetermined non-object region (such as the top plate region 45) included in the first X-ray CT image 51.

Next, in the step S42, the pixel-value substitution function 34a extracts the outline of the object P for each cross-section of the second X-ray CT image 61.

Next, in the step S43, the pixel-value substitution function 34a generates the sinogram 62 (i.e., forward projection data as one-dimensional data) by executing forward projection based on the extracted outline information.

Next, in the step S44, the scattered-ray correction execution function 34b executes scattered-ray correction on each count value by the tail-fitting method based on the forward projection data. Afterward, the processing returns to the step S5 of the main routine in FIG. 8.

According to the above procedure, scattered-ray correction can be executed on each count value by the tail-fitting method based on information on the outline of the object P estimated from the second X-ray CT image 61 (i.e., information on the non-object region 44ct).

Incidentally, when the X-ray CT apparatus 101 has a function equivalent to the pixel-value substitution function 34a, the nuclear medical diagnostic apparatus 10 may not be provided with the pixel-value substitution function 34a. In this case, the processing of the steps S41 to S43 in FIG. 9 is preliminarily executed by the X-ray CT apparatus 101 and forward projection data in which accurate outline information of the object P is included are inputted from the X-ray CT apparatus 101 to the scattered-ray correction execution function 34b.

Figure 10:
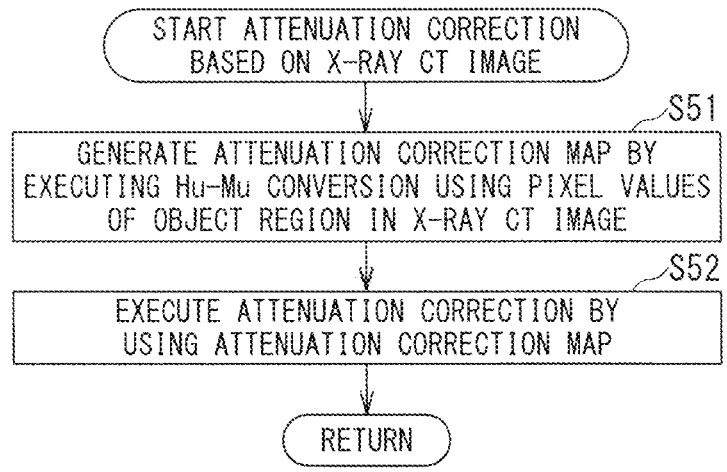
FIG. 10 is a subroutine flowchart of the attenuation correction in the step S5 of FIG. 8 executed by an attenuation correction function based on the first or second X-ray CT image.

FIG. 10 is a subroutine flowchart of the attenuation correction in the step S5 of FIG. 8 executed by the attenuation correction function 35 based on the first X-ray CT image 51 or the second X-ray CT image 61.

This subroutine starts when the nuclear medical diagnostic apparatus 10 acquires the first X-ray CT image 51 from the X-ray CT apparatus 101. The first X-ray CT image 51 may be preliminarily acquired from the X-ray CT apparatus 101 and be stored in the memory circuit 23 prior to start of the processing shown in FIG. 8, for example. Hereinafter, an example of a case where the attenuation correction function 35 executes attenuation correction based on the first X-ray CT image 51 will be explained.

First, in the step S51, the attenuation map generation function 35a generates a gamma-ray attenuation coefficient map (i.e., attenuation map) of the object P by executing Hu-Mu conversion with the use of pixel values of the object region depicted in the first X-ray CT image 51.

Next, in the step S52, the attenuation-correction execution function 35b executes attenuation correction on the gamma-ray emission data based on the attenuation map. Afterward, the processing returns to the step S6 of the main routine in FIG. 8.

According to the above procedure, an attenuation map can generated based on the first X-ray CT image 51 or the second X-ray CT image 61 and attenuation correction can be executed.

Incidentally, the nuclear medical diagnostic apparatus 10 may not be provided with the attenuation map generation function 35a, when an attenuation map can be obtained without generating it (e.g., when the X-ray CT apparatus 101 has a function equivalent to the attenuation map generation function 35a, when an attenuation map can be acquired via the network 100, and when an attenuation map is preliminarily stored in the memory circuit 23). In this case, the step S51 in FIG. 10 is not executed and an attenuation map may be inputted to the attenuation-correction execution function 35b from the X-ray CT apparatus 101 or from another apparatus via the network 100. Additionally, in this case, an attenuation map may be preliminarily stored in the memory circuit 23 and be read out and used by the attenuation-correction execution function 35b.

Next, the pixel-value substitution executed in the step S41 in FIG. 9 will be explained. Hereinafter, an example of a case where the predetermined non-object region is the top plate region 45 and the predetermined pixel value is a pixel value corresponding to an HU value −1000 of the air 46 will be explained.

Figure 11:
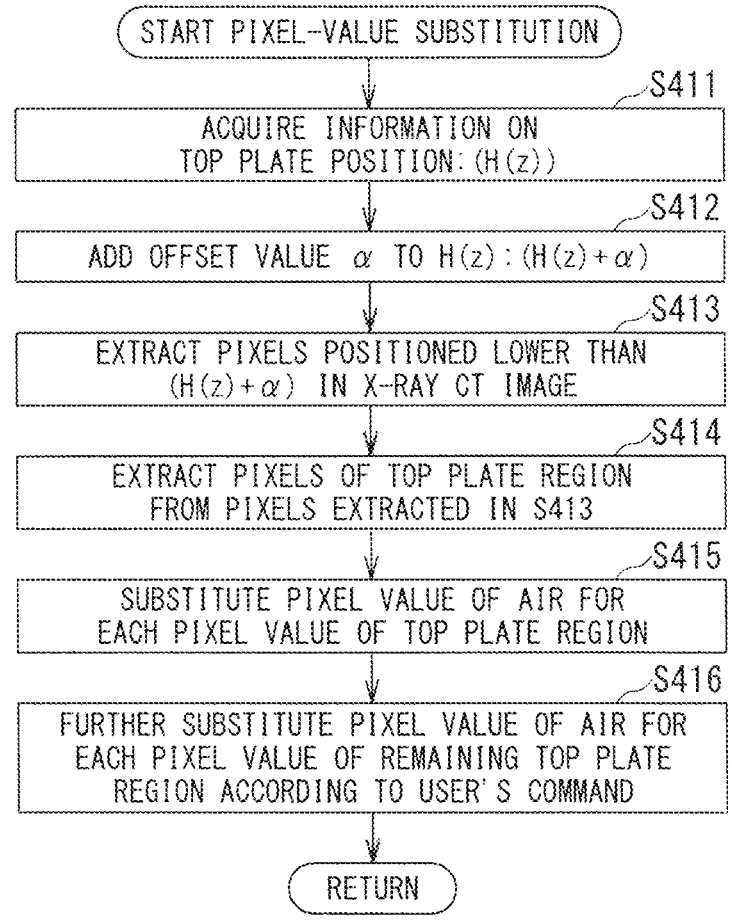
FIG. 11 is a subroutine flowchart of the first process of the pixel-value substitution executed in the step S41 of FIG. 9.

FIG. 11 is a subroutine flowchart of the first process of the pixel-value substitution executed in the step S41 of FIG. 9.

Figure 12A:
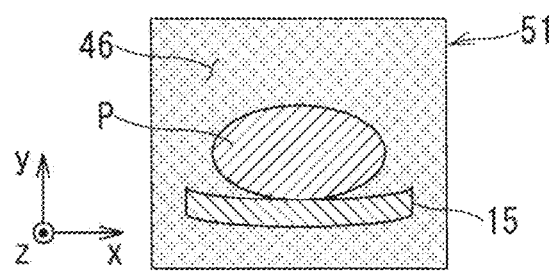
FIG. 12A is a schematic diagram showing an example of the first X-ray CT image for explaining the first process of the pixel-value substitution.

FIG. 12A is a schematic diagram showing an example of the first X-ray CT image 51 for explaining the first process of the pixel-value substitution.

Figure 12B:
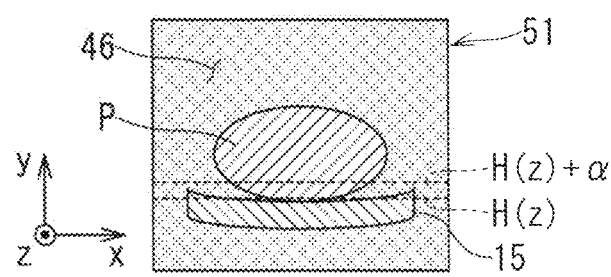
FIG. 12B is a schematic diagram showing an example of setting a guideline in the first process.

FIG. 12B is a schematic diagram showing an example of setting a guideline in the first process.

Figure 12C:
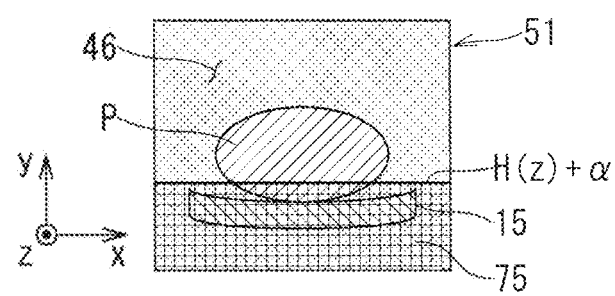
FIG. 12C is a schematic diagram showing an example of an image region below the guideline determined in the first process.

FIG. 12C is a schematic diagram showing an example of an image region 75 below the guideline determined in the first process.

Figure 12D:
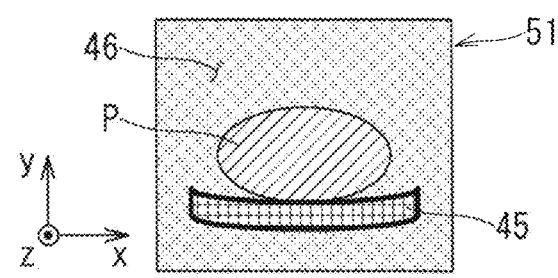
FIG. 12D is a schematic diagram showing an example of a top plate region extracted in the first process.

FIG. 12D is a schematic diagram showing an example of the top plate region 45 extracted in the first process.

Figure 12E:
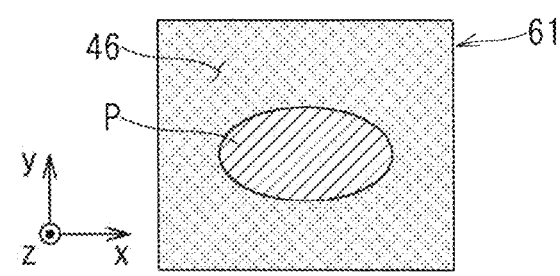
FIG. 12E is a schematic diagram showing an example of the second X-ray CT image generated in the first process.

FIG. 12E is a schematic diagram showing an example of the second X-ray CT image 61 generated in the first process.

The first process of the pixel-value substitution is a process in the case of acquiring positional information of the top plate 15 from the X-ray CT apparatus 101.

In the step S411, the pixel-value substitution function 34a of the nuclear medical diagnostic apparatus 10 acquires positional information of the top plate 15 from the X-ray CT apparatus 101, and calculates the height H(z) of the top plate 15 in the first X-ray CT image 51. Specifically, the X-ray CT apparatus 101 can generate the positional information of the top plate 15 to be inputted to the nuclear medical diagnostic apparatus 10, based on output of an encoder mounted on a motor configured to drive the top plate 15 and information on the height of the top plate 15 included in the corresponding X-ray scan plan, for example.

Incidentally, the positional information of the top plate 15 acquired from the X-ray CT apparatus 101 may be information of a value being constant in the z-axis direction (i.e., in the body axis direction of object P) and/or information of a value according to the position in the z-axis direction. Even if the positional information of the top plate 15 acquired from the X-ray CT apparatus 101 is a constant value in the z-axis direction, the pixel-value substitution function 34a may calculate the height H(z) of the top plate 15 according to the position in the z-axis direction. This calculation of the height H(z) of the top plate 15 can be executed based on, for example, information on the weight of the object P and information on the moving distance of the top plate 15 from the reference position of its supporting platform.

Next, in the step S412, the pixel-value substitution function 34a generates a guideline H(z)+α obtained by adding an offset α to the height H(z) of the top plate 15 (see FIG. 12B).

Next, in the step S413, the pixel-value substitution function 34a extracts pixels positioned lower than the guideline H(z)+α in the first X-ray CT image 51 (see FIG. 12C).

Next, in the step S414, the pixel-value substitution function 34a extracts pixels of the top plate 15 from the pixels extracted in the step S413 (see FIG. 12D).

Next, in the step S415, the pixel-value substitution function 34a generates the second X-ray CT image 61 by substituting a pixel value of the air 46 for each pixel value of the top plate region 45 (see FIG. 12E).

Next, in the step S416, when a user's command to execute further pixel-value substitution is inputted via the input circuit 21, the pixel-value substitution function 34a further substitutes the pixel value of the air 46 for a pixel value of each remaining pixel of the top plate region 45 according to the inputted command. Afterward, the process proceeds to the step S42 in FIG. 9.

By executing the first process of the pixel-value substitution, the second X-ray CT image 61 can be generated by substituting the pixel value of the air 46 for each pixel value of the top plate region 45 based on the positional information of the top plate 15 acquired from the X-ray CT apparatus 101.

Figure 13:
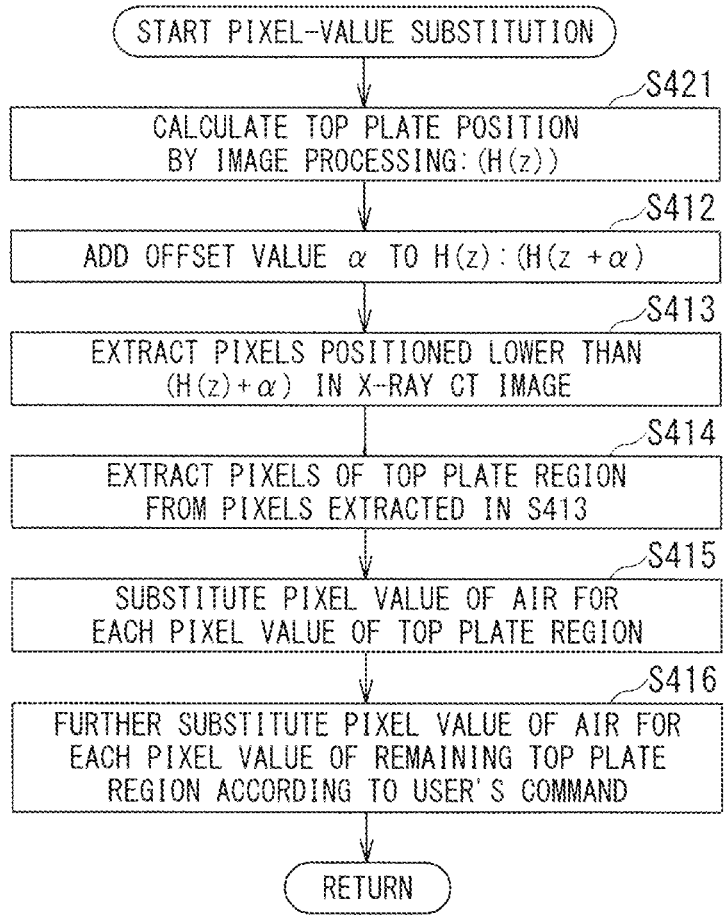
FIG. 13 is a subroutine flowchart of the second process of the pixel-value substitution executed in the step S41 of FIG. 9.

FIG. 13 is a subroutine flowchart of the second process of the pixel-value substitution executed in the step S41 of FIG. 9.

The second process of the pixel-value substitution is a process in the case of calculating the positional information of the top plate 15 by executing image processing on the first X-ray CT image 51. In FIG. 13, the same step number is given for each step equivalent to one of the steps explained in FIG. 11 and duplicate explanation is omitted.

In the step S421, the pixel-value substitution function 34a extracts the region of the top plate 15 by executing image processing such as pattern matching on the original three-dimensional data of the first X-ray CT image 51, and thereby calculates the height H(z) of the top plate 15 for each cross-section.

By executing the second process of the pixel-value substitution shown in FIG. 13, the second X-ray CT image 61 can be generated by substituting the pixel value of the air 46 for each pixel value of the top plate region 45 based on the positional information of the top plate 15 acquired by executing image processing on the first X-ray CT image 51. According to the second process, the height H(z) of the top plate 15 can be directly determined from the first X-ray CT image 51 without acquiring the positional information of the top plate 15 from the X-ray CT apparatus 101.

Figure 14:
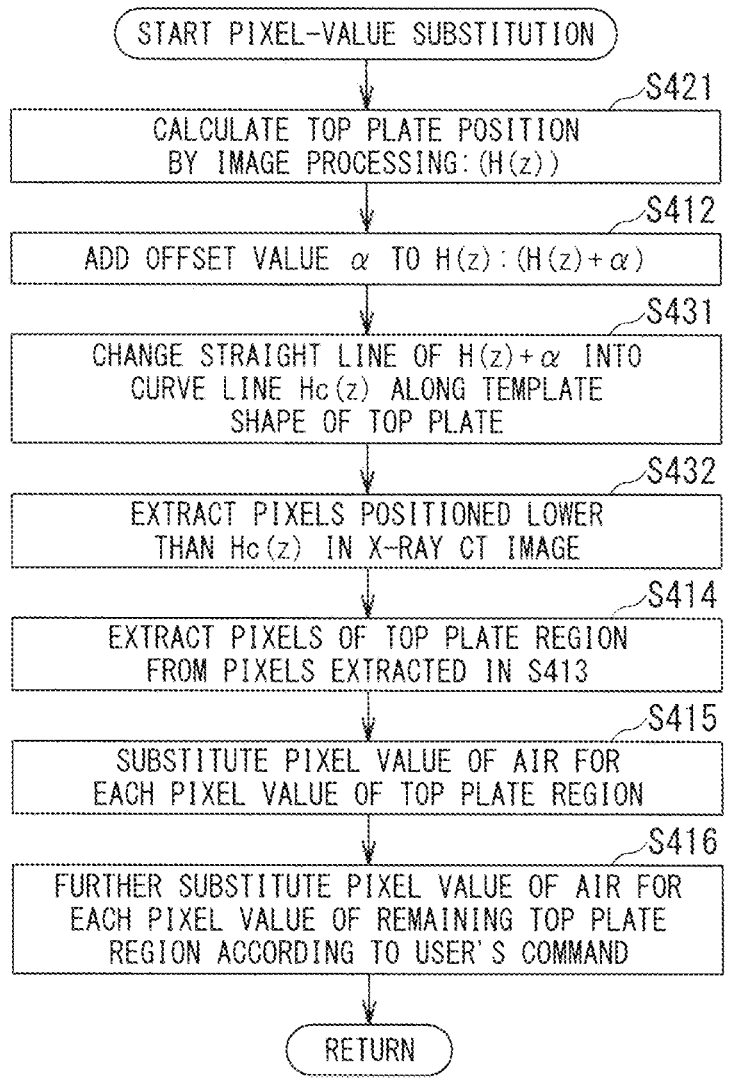
FIG. 14 is a subroutine flowchart of the third process of the pixel-value substitution executed in the step S41 of FIG. 9.

FIG. 14 is a subroutine flowchart of the third process of the pixel-value substitution executed in the step S41 of FIG. 9.

Figure 15A:
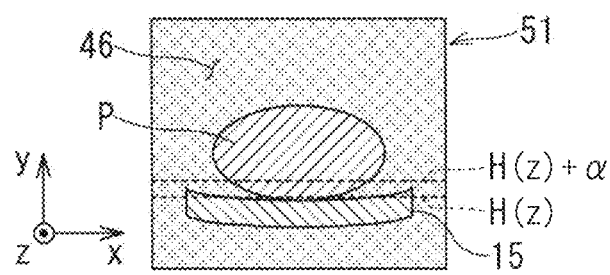
FIG. 15A is a schematic diagram showing an example of setting a guideline in the first process.

FIG. 15A is a schematic diagram showing an example of setting a guideline in the first process.

Figure 15B:
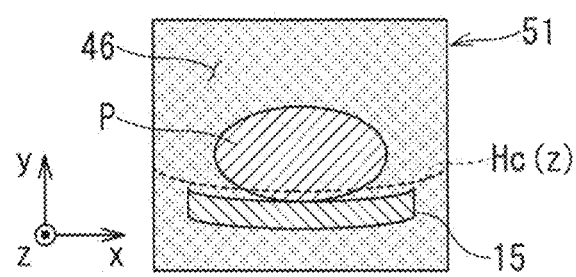
FIG. 15B is a schematic diagram showing an example of setting a guideline in the third process.

FIG. 15B is a schematic diagram showing an example of setting a guideline in the third process.

Figure 15C:
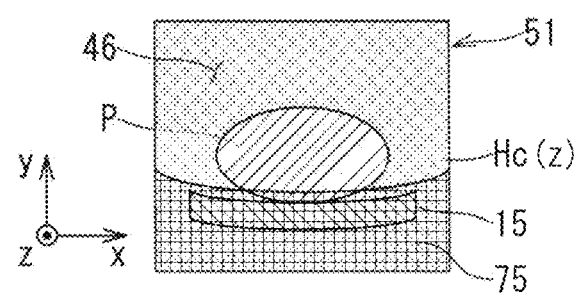
FIG. 15C is a schematic diagram showing an example of an image region below the guideline determined in the third process.

FIG. 15C is a schematic diagram showing an example of the image region 75 below the guideline determined in the third process.

Figure 15D:
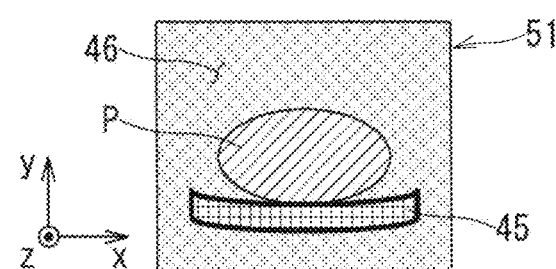
FIG. 15D is a schematic diagram showing an example of a top plate region extracted in the third process.

FIG. 15D is a schematic diagram showing an example of the top plate region 45 extracted in the third process.

Figure 15E:
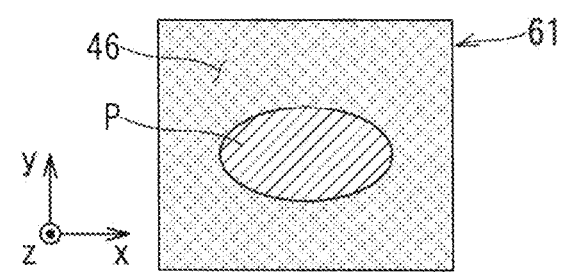
FIG. 15E is a schematic diagram showing an example of the second X-ray CT image generated in the third process.

FIG. 15E is a schematic diagram showing an example of the second X-ray CT image 61 generated in the third process.

The third process of the pixel-value substitution is a process in a case where the positional information of the top plate 15 is calculated by executing image processing on the first X-ray CT image 51 and a guideline is set as a curve line along the template shape of the top plate 15.

When the guideline H(z)+α is generated in the step S412 in FIG. 14, in the next step S431, the pixel-value substitution function 34a changes the straight line of the guideline into a curve line along the template shape of the top plate 15 (see FIG. 15B). The template shape of the top plate 15 may be preliminarily stored in the memory circuit 23 and/or acquired via the network 100.

In the next step S432, the pixel-value substitution function 34a extracts pixels positioned lower than the guideline Hc(z) in the first X-ray CT image 51 (see FIG. 15C).

In the next step S414, the pixel-value substitution function 34a extracts pixels of the top plate region 45 from the pixels extracted in the above step S432 (see FIG. 15D).

In the next step S415, the pixel-value substitution function 34a generates the second X-ray CT image 61 by substituting the pixel value of the air 46 for each pixel value of the top plate region 45 (see FIG. 15E).

In addition, when a user's command to execute further pixel-value substitution is inputted via the input circuit 21, the pixel-value substitution function 34a further substitutes the pixel value of the air 46 for a pixel value of each remaining pixel of the top plate region 45 in the second X-ray CT image 61 in the next the step S416. Afterward, the process proceeds to the step S42 in FIG. 9.

By executing the third process of the pixel-value substitution shown in FIG. 14, the second X-ray CT image 61 can be generated by setting a guideline along the template shape of the top plate 15 based on the positional information of the top plate 15 obtained by executing image processing on the first X-ray CT image 51 and then substituting the pixel value of the air 46 for each pixel value of the top plate region 45.

According to the third process, the height H(z) of the top plate 15 can be directly determined from the first X-ray CT image 51 without acquiring the positional information of the top plate 15 from the X-ray CT apparatus 101. In addition, since the guideline can be set as a curve line along the template shape of the top plate 15, the top plate region 45 can be infallibly included in the extracted region 75 and can reliably reduce extraction omission of pixels of the top plate region 45.

By executing any one of the first to third processes of the pixel-value substitution, the second X-ray CT image 61 can be generated by substituting the pixel value of the air 46 for a pixel value of each pixel of the top plate region 45. In addition, flexure of the top plate 15 due to weight of the object P can be easily reflected on the second X-ray CT image 61 by using the height H(z) according to the z-axis position of the top plate 15.

Moreover, other than the first to third processes of the pixel-value substitution, when a scanogram of the object P can be acquired as an example, the pixel-value substitution function 34a may calculate the height H(z) of the top plate 15 by executing image processing on this scanogram. Especially when a scanogram is an image obtained by fluoroscopic imaging of a y-z plane and the whole image of the top plate 15 along the z-axis direction is included in this scanogram, the pixel-value substitution function 34a can easily and accurately calculate the height H(z) of the top plate 15 according to its z-axis position.

Further, the x-y position of the pixels of the top plate 15 in the first X-ray CT image 51 (i.e., the top plate position in the image) extracted in the step S414 may be stored in the memory circuit 23 in association with information on the z position of the slice image used for extracting this top plate position in the image. In this case, the information on the top plate position in the image stored in the memory circuit 23 can be used for extracting pixels corresponding to the top plate 15 in another slice image.

For example, when the position of the top plate 15 is expressed by values being constant in the z-axis direction, it is considered that the top plate position in the image is common to plural slices. When the pixel-value substitution is executed on another slice in this case, the step S411 (or S421) to the step S413 may be omitted and the pixel-value substitution function 34a may acquire the top plate position in the image from the memory circuit 23 in the step S414. Then, the pixel-value substitution function 34a can generate the second X-ray CT image 61 by substituting the pixel value of the air 46 for each pixel value of the top plate region 45 in the step S415.

Furthermore, when the positional information of the top plate 15 is information on a value according to its position in the z-axis direction, the information on the top plate position in the image acquired from the memory circuit 23 may be corrected according to the information on the z-axis position of the current target slice. The same holds true for a case where the pixel-value substitution function 34a can acquire information on the weight of the object P and the information on the moving distance of the top plate 15 from the reference position of its supporting platform and can calculate the height H(z) of the top plate 15 according to its position in the z-axis direction.

The nuclear medical diagnostic apparatus 10 of the present embodiment generates an X-ray CT image (i.e., the second X-ray CT image 61) subjected to pixel value substitution, by substituting a predetermined pixel value (e.g., the pixel value corresponding to an HU value −1000 of the air 46) for each pixel value of a predetermined non-object region (e.g., the top plate region 45) in the first X-ray CT image 51. Then, on the basis of the forward projection data obtained by forward projection of the second X-ray CT image 61, scattered-ray correction can be executed on each count value by the tail-fitting method.

A region which is not supposed to include any RI and has a CT value different from that of the air region 47 (e.g., the top plate region 45) can be more reliably included in the non-object region 44ct by extracting the outline of the object P with the use of this second X-ray CT image 61 than a case of using the first X-ray CT image 51. In other words, the non-object region 44 can be more accurately estimated by using the second X-ray CT image 61 than the case of using the first X-ray CT image 51.

Hence, the nuclear medical diagnostic apparatus 10 can more widely secure the non-object region 44 by executing the scattered-ray correction based on the second X-ray CT image 61. Thus, sufficient number of pixels can be secured for a tail region (i.e., a scattered-ray region). According to the nuclear medical diagnostic apparatus 10 as mentioned above, since estimation accuracy of scattered rays can be improved, contrast of a nuclear medical image is improved, quantitative property of a nuclear medical image is improved, and thereby diagnostic efficiency based on a nuclear medical image is improved.

Second Embodiment

Next, the nuclear medical diagnostic apparatus and the image processing method of the second embodiment will be explained.

Figure 16:
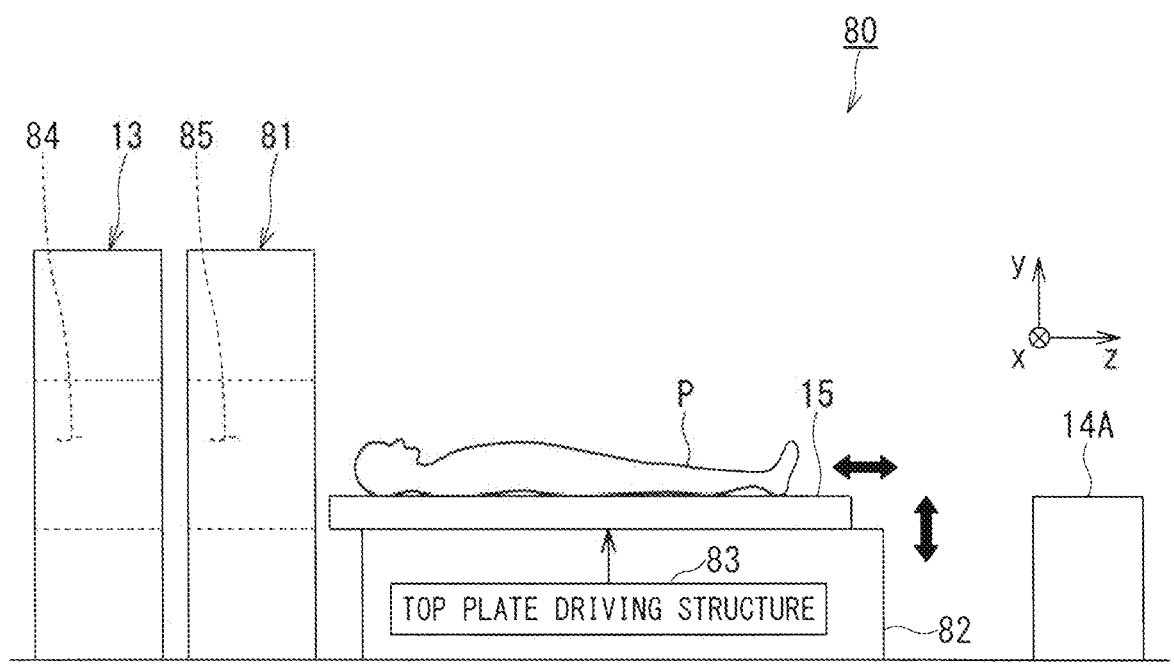
FIG. 16 is an outline view showing an example of a composite apparatus including a nuclear medical diagnostic apparatus of the second embodiment.

FIG. 16 is an outline view showing an example of the composite apparatus 80 including the nuclear medical diagnostic apparatus 10A of the second embodiment.

Figure 17:
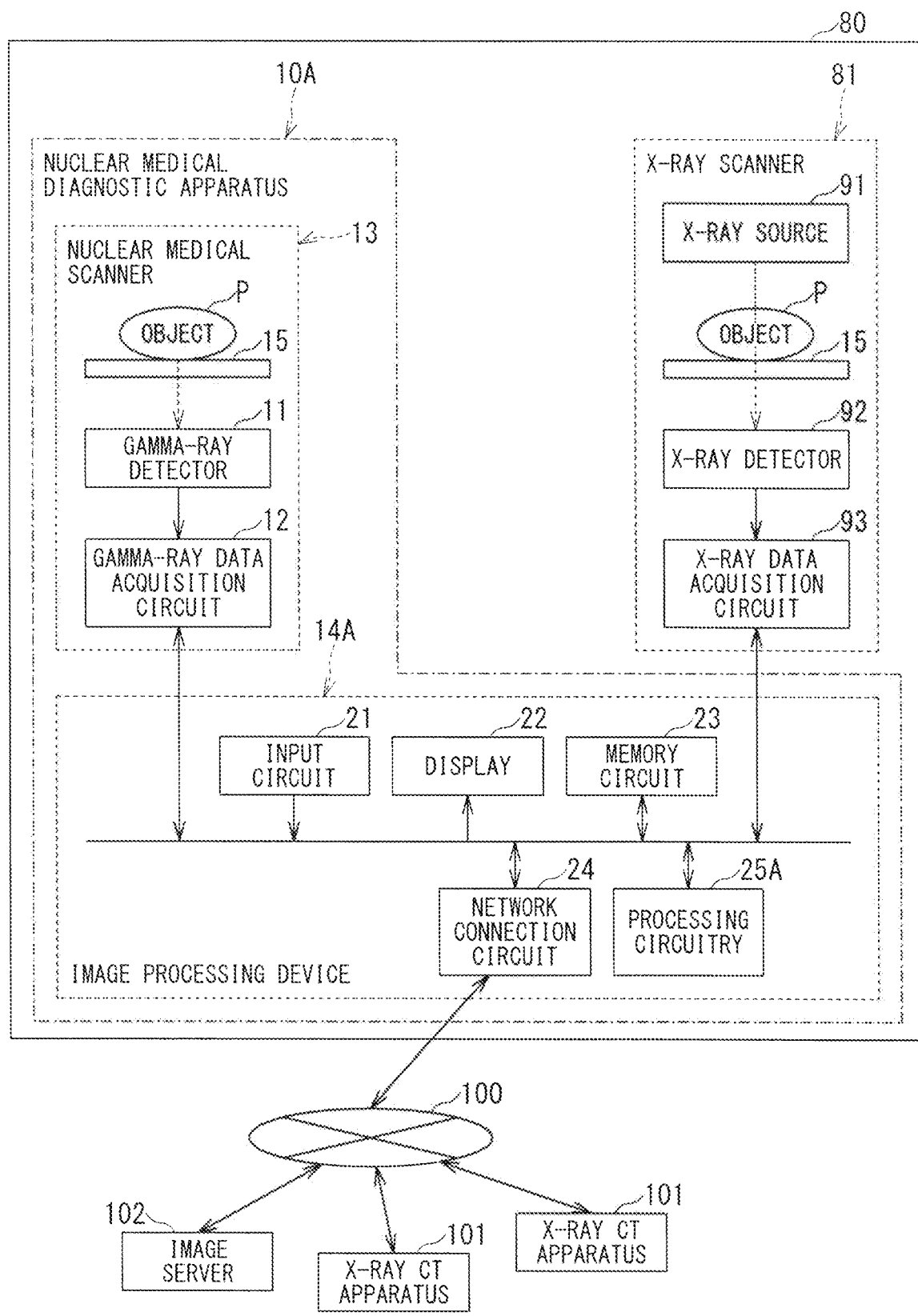
FIG. 17 is a general block diagram showing an example of configuration of the composite apparatus including the nuclear medical diagnostic apparatus of the second embodiment.

FIG. 17 is a general block diagram showing an example of configuration of the composite apparatus 80 including the nuclear medical diagnostic apparatus 10A of the second embodiment.

The nuclear medical diagnostic apparatus 10A of the second embodiment is different from the first embodiment in that the nuclear medical diagnostic apparatus 10A constitutes the composite apparatus 80 in combination with an X-ray CT apparatus such as a PET-CT apparatus and a SPECT-CT apparatus. Since all the other points in configuration and operations of the nuclear medical diagnostic apparatus 10A are not substantially different from the nuclear medical diagnostic apparatus 10 explained in FIG. 1, the same reference symbols are given for identical components in each figure, and duplicate explanation is omitted.

As shown in FIG. 16, the composite apparatus 80 includes an X-ray scanner 81, a bed 82 equipped with the top plate 15, and a top plate driving structure 83 in addition to the nuclear medical scanner 13 and an image processing device 14A of the nuclear medical diagnostic apparatus 10A.

The nuclear medical scanner 13 and the X-ray scanner 81 includes a cylindrical bore 84 and a cylindrical bore 85 into each of which the top plate 15 is moved, respectively.

The top plate driving structure 83 moves the top plate 15 upward and downward along the y-axis under the control of the image processing device 14A. Further, the top plate driving structure 83 horizontally moves the top plate 15 to an X-ray irradiation field in the bore 85 and/or a gamma-ray irradiation field in the bore 84 along the z-axis, under the control of the image processing device 14A.

As shown in FIG. 17, the image processing device 14A includes the input circuit 21, the display 22, the memory circuit 23, the network connection circuit 24, and processing circuitry 25A.

In addition, as shown in FIG. 17, the X-ray scanner 81 includes an X-ray source 91, an X-ray detector 92, and an X-ray data acquisition circuit 93.

The X-ray source 91 includes an X-ray tube and a diaphragm. The X-ray tube is applied with high-voltage by a high-voltage power supply and generates X-rays. X-rays generated by the X-ray tube are emitted as, for example, an X-ray fan beam or an X-ray cone beam toward the object P. The diaphragm adjusts an irradiation range in the slice direction of X-rays emitted from the X-ray tube, under the control of the image processing device 14A.

The X-ray detector 92 is configured of one or plural X-ray detection elements (i.e., charge accumulation elements). Each X-ray detection element detects X-rays emitted from the X-ray tube. The X-ray source 91 and the X-ray detector 92 are supported by a rotating body so that the X-ray source 91 and the X-ray detector 92 face each other with the object P loaded on the top plate 15 interposed therebetween.

As the X-ray detector 92, for example, a so-called one-dimensional array type detector (i.e., a single slice type detector) which includes one column of detection elements in a slice direction may be used. In addition, a so-called two-dimensional array type detector (i.e., a multi-slice type detector) which includes plural rows of X-ray detection elements arrayed in the channel direction and plural columns of X-ray detection elements arrayed in the slice direction may be used as the X-ray detector 92.

The X-ray data acquisition circuit 93 amplifies signals of transmission data detected by the respective X-ray detection elements of the X-ray detector 92, converts the amplified signals into digital signals, and outputs the digitized data to the image processing device 14A as X-ray projection data.

The rotating body integrally supports the X-ray source 91, the X-ray detector 92, and the X-ray data acquisition circuit 93. The rotating body rotates under the control of the image processing device 14A, and thereby the X-ray source 91, the X-ray detector 92, and the X-ray data acquisition circuit 93 integrally rotate around the object P.

Figure 18:
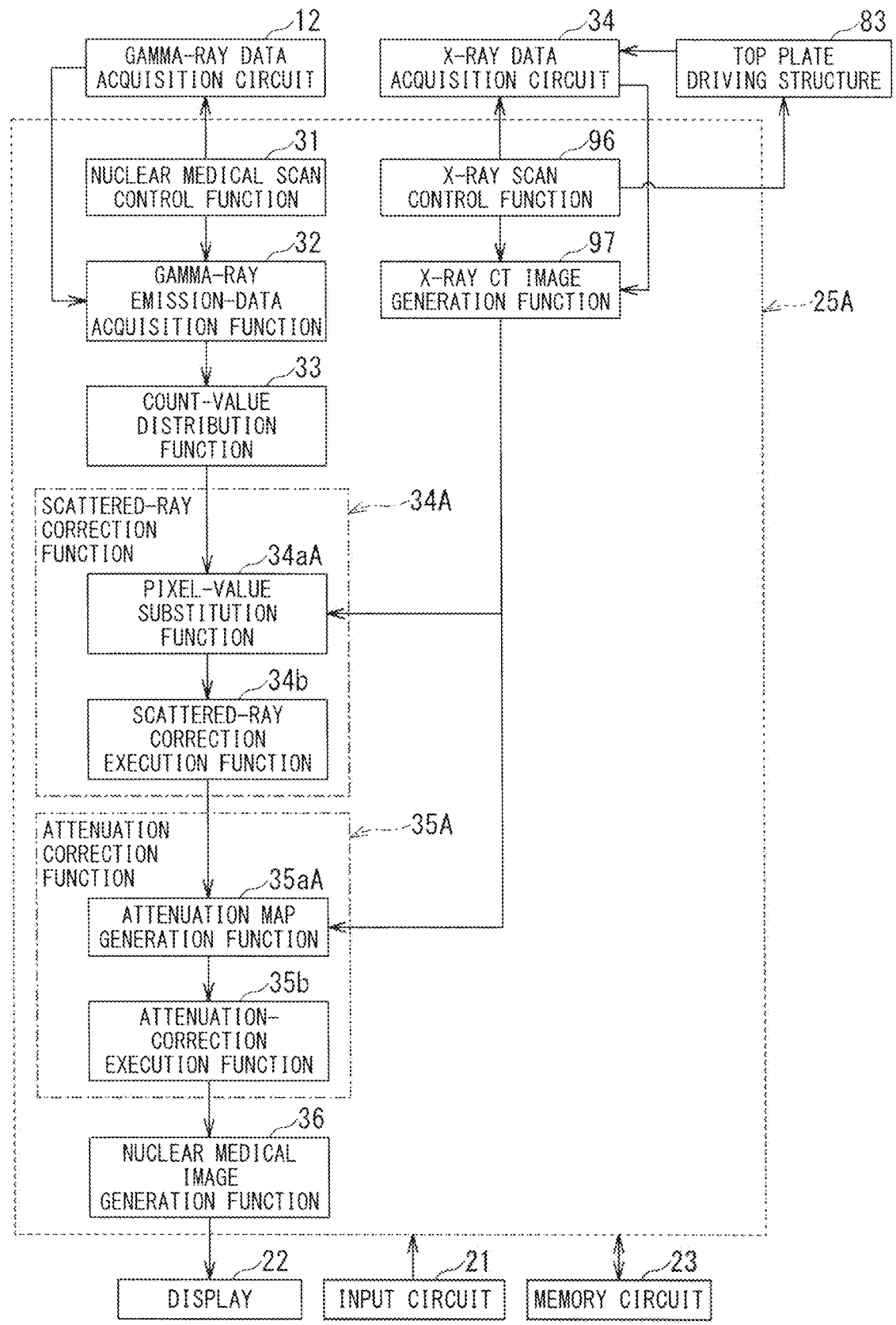
FIG. 18 is a general block diagram showing an example of functions implemented by a processor of processing circuitry of the second embodiment.

FIG. 18 is a general block diagram showing an example of functions implemented by a processor of the processing circuitry 25A of the second embodiment.

As shown in FIG. 18, the processor of the processing circuitry 25A functions as at least the nuclear medical scan control function 31, the gamma-ray emission-data acquisition function 32, the count-value distribution function 33, a scattered-ray correction function 34A, an attenuation correction function 35A, the nuclear medical image generation function 36, an X-ray scan control function 96, and an X-ray CT image generation function 97 by image processing program stored in memory media including a ROM. Each of those functions is stored in the form of a program in the memory media.

The X-ray scan control function 96 receives a command to execute a scan plan via the input circuit 21 from a user and controls the X-ray scanner 81 so that the X-ray scanner 81 executes a scan based on the scan plan. The X-ray projection data acquired by the scan are inputted from the X-ray data acquisition circuit 93 to the X-ray CT image generation function 97.

Output of an encoder mounted on a motor of the top plate driving structure 83 may be acquired in association with the X-ray projection data by the X-ray data acquisition circuit 93 and be inputted to the processing circuitry 25A. Additionally, the output of the encoder may be directly inputted to the processing circuitry 25A without going through the X-ray data acquisition circuit 93. Further, when the pixel-value substitution function 34aA of the scattered-ray correction function 34A does not use the first process of the pixel-value substitution as explained in FIG. 11, the output of the encoder of the top plate driving structure 83 may not be inputted to the processing circuitry 25A.

The X-ray CT image generation function 97 generates the first X-ray CT image 51 based on the X-ray projection data and inputs the first X-ray CT image 51 to the scattered-ray correction function 34A and the attenuation correction function 35A.

The pixel-value substitution function 34aA of the scattered-ray correction function 34A generates the second X-ray CT image 61 by executing pixel-value substitution on the first X-ray CT image 51 generated by the X-ray CT image generation function 97, in the step S41 of FIG. 9.

The attenuation map generation function 35aA of the attenuation correction function 35A generates a gamma-ray attenuation coefficient map (i.e., an attenuation map) of the object P by executing Hu-Mu conversion with the use of pixel values of the object region depicted in the first X-ray CT image 51 generated by the X-ray CT image generation function 97, in the step S51 of FIG. 10.

The same effects as the nuclear medical diagnostic apparatus 10 of the first embodiment can also be obtained by the nuclear medical diagnostic apparatus 10A of the second embodiment. Further, since the composite apparatus 80 equipped with the nuclear medical diagnostic apparatus 10A of the second embodiment includes the X-ray scanner 81, it can easily acquire X-ray projection data and gamma-ray emission data of the same region of the same object P.

According to at least one of the above-described embodiments, scattered-ray correction can be appropriately executed by the tail-fitting method with the use of the non-object region 44ct accurately estimated from the second X-ray CT image 61.

The processing circuitry in the above-described embodiment is an example of the processing circuitry described in the claims. In addition, the term "processor" in the above-described embodiments means, for instance, a circuit such as a special-purpose or general-purpose CPU (Central Processing Unit), a special-purpose or general-purpose GPU (Graphics Processing Unit), an ASIC (Application Specific Integrated Circuit), a programmable logic device including an SPLD (Simple Programmable Logic Device) and a CPLD (Complex Programmable Logic Device) as examples, and an FPGA (Field Programmable Gate Array). A processor implements various types of functions by reading out programs stored in a memory circuit and executing the programs.

In addition, programs may be directly installed in the circuit of a processor instead of storing programs in the memory circuit. In this case, the processor implements various types of functions by reading out programs stored in its own circuit and executing the programs. Moreover, each function of the processing circuitry may be implemented by processing circuitry configured of a single processor. Further, the processing circuitry may be configured by combining plural processors independent of each other so that each function of the processing circuitry is implemented by causing each processor to execute the corresponding program. When plural processors are provided for the processing circuitry, a memory circuit for storing the programs may be provided for each processor or one memory circuit may collectively store all the programs corresponding to all the processors.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

For example, the processing circuitry 25 of the nuclear medical diagnostic apparatus 10 of the first embodiment may be provided with the X-ray CT image generation function 97 of the processing circuitry 25A of the second embodiment. In this case, the processing circuitry 25 may acquire X-ray projection data from the X-ray CT apparatus 101 so as to generate the first X-ray CT image 51 based on the acquired X-ray projection data.

In addition, each scattered-ray correction function (34 and 34A) may implement scattered-ray correction by combining two or more scattered-ray correction methods using energy windows such as the above-described tail-fitting method, the DEW method, and the TEW method.

Further, although an example of processing the steps of the flowchart is described in the embodiments in which each steps are time-sequentially performed in order along the flowchart, each step of the flowchart may not be necessarily processed in a time series, and may be executed in parallel or individually executed.

The invention claimed is:

1. A nuclear medical diagnostic apparatus comprising: processing circuitry configured to:
    acquire gamma-ray emission data based on gamma rays emitted from radio isotopes administered to an object;
    obtain a first X-ray CT image by imaging the object;
    perform image processing on the first X-ray CT image to
        estimate a position of a non-object region in the first X-ray CT image;
        extract the non-object region from the first X-ray CT image based on the estimated position of the non-object region;
    obtain a second X-ray CT image by replacing pixel values of the extracted non-object region in the first X-ray CT image with a predetermined pixel value to increase a number of pixels in a tail region that corresponds to a scattering region where any radioactivity is not supposed to exist;
    estimate a scattered ray distribution by approximating the tail region in which the number of the pixels are increased; and
    execute scattered-ray correction on the gamma-ray emission data based on the second X-ray CT image by a tail fitting method using the scattered ray distribution.

2. The nuclear medical diagnostic apparatus according to claim 1, wherein the processing circuitry is configured to execute the scattered-ray correction on the gamma-ray emission data based on forward projection data obtained by performing forward projection on the second X-ray CT image.

3. The nuclear medical diagnostic apparatus according to claim 2, wherein the processing circuitry is configured to generate the forward projection data by performing the forward projection on the second X-ray CT image.

4. The nuclear medical diagnostic apparatus according to claim 1, wherein the non-object region is an imaging region of a top plate included in the first X-ray CT image and the predetermined pixel value is a pixel value corresponding to a CT value of air.

5. The nuclear medical diagnostic apparatus according to claim 1, wherein the second X-ray CT image is obtained by further replacing pixel values of the extracted non-object region that still remains in the first X-ray CT image with the predetermined pixel value according to a user's command inputted via an input circuit.

6. The nuclear medical diagnostic apparatus according to claim 1, wherein, when the processing circuitry generates the second X-ray CT image from the first X-ray CT image for a predetermined slice, the processing circuitry is configured to store information on a pixel position of the extracted non-object region in the first X-ray CT image in a memory circuit.

7. The nuclear medical diagnostic apparatus according to claim 6, wherein the processing circuitry is configured to generate the second X-ray CT image from the first X-ray CT image for a slice other than the predetermined slice by using the information on the pixel position of the extracted non-object region in the first X-ray CT image stored in the memory circuit.

8. The nuclear medical diagnostic apparatus according to claim 1, wherein the processing circuitry is configured to execute attenuation correction on the gamma-ray emission data based on a gamma-ray attenuation coefficient map of the object generated by using pixel values of a region of the object included in the first X-ray CT image.

9. The nuclear medical diagnostic apparatus according to claim 8, wherein the processing circuitry is configured to generate the gamma-ray attenuation coefficient map of the object by using the pixel values of the region of the object included in the first X-ray CT image.

10. The nuclear medical diagnostic apparatus according to claim 1, wherein the processing circuitry is configured to generate a nuclear medical image based on the gamma-ray emission data subjected to the scattered-ray correction and to display the nuclear medical image on a display.

11. An image processing method comprising:
  acquiring gamma-ray emission data based on gamma rays emitted from radio isotopes administered to an object;
  obtaining a first X-ray CT image by imaging the object;
  performing image processing on the first X-ray CT image to estimate a position of a non-object region in the first X-ray CT image;
  extracting the non-object region from the first X-ray CT image based on the estimated position of the non-object region;
  obtaining a second X-ray CT image by replacing pixel values of the extracted non-object region included in the first X-ray CT image with a predetermined pixel value to increase a number of pixels in a tail region that corresponds to a scattering region where any radioactivity is not supposed to exist;
  estimating a scattered ray distribution by approximating the tail region in which the number of the pixels are increased; and
  executing scattered-ray correction on the gamma-ray emission data based on the second X-ray CT image by a tail fitting method using the scattered ray distribution.

\* \* \* \* \*